(12) United States Patent
Bruton et al.

(10) Patent No.: US 7,638,631 B2
(45) Date of Patent: Dec. 29, 2009

(54) METHYLENE DIPIPERIDINE DERIVATIVES

(75) Inventors: Gordon Bruton, Harlow (GB); Vicky Johnstone, Harlow (GB); Barry Sidney Orlek, Harlow (GB)

(73) Assignee: Glaxo Group Limited, Greenford (GB)

( * ) Notice: Subject to any disclaimer, the term of this patent is extended or adjusted under 35 U.S.C. 154(b) by 148 days.

(21) Appl. No.: 11/575,311

(22) PCT Filed: Sep. 16, 2005

(86) PCT No.: PCT/EP2005/010169

§ 371 (c)(1),
(2), (4) Date: Mar. 15, 2007

(87) PCT Pub. No.: WO2006/029906

PCT Pub. Date: Mar. 23, 2006

(65) Prior Publication Data

US 2008/0108624 A1     May 8, 2008

(30) Foreign Application Priority Data

Sep. 17, 2004   (GB)   ................. 0420831.0

(51) Int. Cl.
  *C07D 401/00* (2006.01)
  *C07D 211/08* (2006.01)
(52) U.S. Cl. ..................... 546/187; 546/192
(58) Field of Classification Search ............... 546/187, 546/192
  See application file for complete search history.

(56) References Cited

U.S. PATENT DOCUMENTS

2003/0119817 A1   6/2003   Mehta et al.

FOREIGN PATENT DOCUMENTS

| JP | 4018071 | 1/1992 |
|----|---------|--------|
| WO | 9937304 A1 | 7/1999 |
| WO | 0059510 A1 | 10/2000 |
| WO | 0107436 A2 | 2/2001 |
| WO | 0232893 A2 | 4/2002 |
| WO | 0243762 A2 | 6/2002 |
| WO | 02072093 A2 | 9/2002 |
| WO | 02079753 A2 | 10/2002 |
| WO | 03031432 A1 | 4/2003 |

OTHER PUBLICATIONS

Giovannini et al.; "Effects of Histamine H3 Receptor Agonists and Antagonists on Cognitive Performance and Scopolamine-Induced Amnesia"; Behav. Brain Res.; 1999; vol. 104; pp. 147-155.
Leurs et al.; "Therapeutic Potential of Histamine H3 Receptor Agonists and Antagonists"; Trends Pharmacol. Sci.; 1998; vol. 19; pp. 177-183.
Onodera et al.; "Histamine H3 Antagonists as Potential Therapeutics in the CNS"; The Histamine H3 Receptor: A Target of New Drugs; 1998; pp. 255-267; Elsevier Science B.V.; The Netherlands.
Schlicker et al.; "Modulation of Neurotransmitter Release via Histamine H3 Heteroreceptors"; Fundam. Clin. Pharmacol.; 1994; vol. 8; pp. 128-137.

*Primary Examiner*—D. Margaret Seaman
*Assistant Examiner*—Nizal S Chandrakumar
(74) *Attorney, Agent, or Firm*—Bonnie L. Deppenbrock

(57) ABSTRACT

The present invention relates to novel methylene dipiperidine derivatives having pharmacological activity, processes for their preparation, to compositions containing them and to their use in the treatment of neurological and psychiatric disorders.

4 Claims, No Drawings

METHYLENE DIPIPERIDINE DERIVATIVES

CROSS-REFERENCE TO RELATED APPLICATIONS

This application is filed pursuant to 35 USC §371 as a U.S. National Phase Application of international Patent Application Ser. No. PCT/EP2005/010169 filed on 16 Sep. 2005, which claims priority from 0420831.0 filed on 17 Sep. 2004 in the United Kingdom.

The present invention relates to novel methylene dipiperidine derivatives having pharmacological activity, processes for their preparation, to compositions containing them and to their use in the treatment of neurological and psychiatric disorders.

BACKGROUND OF THE INVENTION

US 2003/119817 (A. Mehta) describes a series of substituted phenyl oxazolidinone compounds which are claimed to be useful in the treatment of microbial infection. WO 99/37304 (Rhone-Poulenc Rorer Pharmaceuticals Inc) and WO 01/07436 (Aventis Pharmaceuticals Products Inc) both describe a series of substituted oxoazaheterocyclyl Factor Xa inhibitors. WO 2002/79753 (Lion Bioscience AG) describes a series of 2-aminobenzoxazole derivatives which are claimed to be useful in the treatment of melanocortin receptor associated conditions e.g. inflammation. WO 2002/43762 and WO 00/59510 (Pfizer Prod Inc) both describe a series of heterocyclyl substituted pyrimidine derivatives which are claimed to be useful in the treatment of diabetes. JO 4018-071-A (Sumitomo Seiyaku KK) describes a series of bis-piperidine derivatives which are claimed to be acetylcholine esterase inhibitors for the treatment of Alzheimer's disease.

The histamine H3 receptor is predominantly expressed in the mammalian central nervous system (CNS), with minimal expression in peripheral tissues except on some sympathetic nerves (Leurs et al., (1998), Trends Pharmacol. Sci. 19, 177-183). Activation of H3 receptors by selective agonists or histamine results in the inhibition of neurotransmitter release from a variety of different nerve populations, including histaminergic and cholinergic neurons (Schlicker et al., (1994), Fundam. Clin. Pharmacol. 8, 128-137). Additionally, in vitro and in vivo studies have shown that H3 antagonists can facilitate neurotransmitter release in brain areas such as the cerebral cortex and hippocampus, relevant to cognition (Onodera et al., (1998), In: The Histamine H3 receptor, ed Leurs and Timmerman, pp 255-267, Elsevier Science B.V.). Moreover, a number of reports in the literature have demonstrated the cognitive enhancing properties of H3 antagonists (e.g. thioperamide, clobenpropit, ciproxifan and GT-2331) in rodent models including the five choice task, object recognition, elevated plus maze, acquisition of novel task and passive avoidance (Giovanni et al., (1999), Behav. Brain Res. 104, 147-155). These data suggest that novel H3 antagonists and/or inverse agonists such as the current series could be useful for the treatment of cognitive impairments in neurological diseases such as Alzheimer's disease and related neurodegenerative disorders.

SUMMARY OF THE INVENTION

The present invention provides, in a first aspect, a compound of formula (I) or a pharmaceutically acceptable salt thereof:

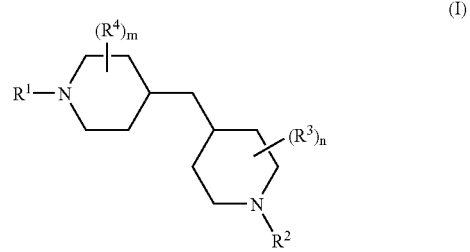

wherein:
$R^1$ represents aryl, heteroaryl, -aryl-X-aryl, -aryl-X-heteroaryl, -aryl-X-heterocyclyl, -heteroaryl-X-heteroaryl, -heteroaryl-X-aryl or -heteroaryl-X-heterocyclyl;
wherein said aryl, heteroaryl and heterocyclyl groups of $R^1$ may be optionally substituted by one or more (e.g. 1, 2 or 3) substituents which may be the same or different, and which are selected from the group consisting of halogen, hydroxy, cyano, nitro, oxo, $haloC_{1-6}$ alkyl, $polyhaloC_{1-6}$ alkyl, $haloC_{1-6}$ alkoxy, $polyhaloC_{1-6}$ alkoxy, $C_{1-6}$ alkyl, $C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, $C_{1-6}$ alkylsulfonamido$C_{1-6}$ alkyl, $C_{1-6}$ alkylamido$C_{1-6}$ alkyl, phenyl, phenylsulfonyl, phenylsulfonyloxy, phenyloxy, phenylsulfonamido, phenylcarboxamido, phenoyl, or a group $—COR^{15}$, $—COOR^{15}$, $NR^{15}R^{16}$, $—CONR^{15}R^{16}$, $—NR^{15}COR^{16}$, $—NR^{15}SO_2R^{16}$ or $—SO_2NR^{15}R^{16}$, wherein $R^{15}$ and $R^{16}$ independently represent hydrogen, $C_{1-6}$ alkyl, $haloC_{1-6}$ alkyl, $polyhaloC_{1-6}$ alkyl or $C_{3-6}$ cycloalkyl or together form a heterocyclic ring;
X represents a bond, O, CO, $SO_2$, $OCH_2$ or $CH_2O$;
$R^2$ represents $C_{1-8}$ alkyl, $C_{3-6}$ alkenyl, $C_{3-6}$ alkynyl, $C_{3-6}$ cycloalkyl, $C_{5-6}$ cycloalkenyl or $—C_{1-4}$alkyl-$C_{3-6}$ cycloalkyl;
wherein said $C_{3-6}$ cycloalkyl groups of $R^2$ may be optionally substituted by one or more (e.g. 1, 2 or 3) substituents which may be the same or different, and which are selected from the group consisting of halogen, $C_{1-4}$ alkyl or poly$haloC_{1-6}$ alkyl groups;
each $R^3$ and $R^4$ group independently represents $C_{1-4}$ alkyl;
m and n independently represents 0, 1 or 2;

or solvates thereof.

In one aspect, the invention provides compounds of formula (I) wherein:
$R^1$ represents aryl, heteroaryl,-aryl-X-aryl, -aryl-X-heteroaryl, -aryl-X-heterocyclyl, -heteroaryl-X-heteroaryl, -heteroaryl-X-aryl or -heteroaryl-X-heterocyclyl;
wherein said aryl, heteroaryl and heterocyclyl groups of $R^1$ may be optionally substituted by one or more (e.g. 1, 2 or 3) substituents which may be the same or different, and which are selected from the group consisting of halogen, hydroxy, cyano, nitro, oxo, $haloC_{1-6}$ alkyl, $polyhaloC_{1-6}$ alkyl, $haloC_{1-6}$alkoxy, $polyhaloC_{1-6}$ alkoxy, $C_{1-6}$ alkyl, $C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, $C_{1-6}$ alkanoyl, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, $C_{1-6}$ alkylsulfonamido$C_{1-6}$ alkyl, $C_{1-6}$ alkylamido$C_{1-6}$ alkyl, aryl, arylsulfonyl, arylsulfonyloxy, aryloxy, arylsulfonamido, arylcarboxamido, aroyl, or a group $—COR^{15}$, $—COOR^{15}$, $NR^{15}R^{16}$, $—CONR^{15}R^{16}$, $—NR^{15}COR^{16}$, $—NR^{15}SO_2R^{16}$ or $—SO_2NR^5R^{16}$, wherein $R^{15}$ and $R^{15}$ independently represent hydrogen, $C_{1-6}$ alkyl, halo$C_{1-6}$ alkyl, polyhalo$C_{1-6}$ alkyl or $C_{3-6}$ cycloalkyl or together form a heterocyclic ring;

X represents a bond, O, CO, SO$_2$, OCH$_2$ or CH$_2$O;

$R^2$ represents $C_{3-8}$ alkyl, $C_{3-6}$ alkenyl, $C_{3-6}$ alkynyl, $C_{3-6}$ cycloalkyl, $C_{5-6}$cycloalkenyl or —$C_{1-4}$alkyl-$C_{3-6}$ cycloalkyl;

wherein said $C_{3-6}$ cycloalkyl groups of $R^2$ may be optionally substituted by one or more (e.g. 1, 2 or 3) substituents which may be the same or different, and which are selected from the group consisting of halogen, $C_{1-4}$ alkyl or polyhalo$C_{1-6}$ alkyl groups;

each $R^3$ and $R^4$ group independently represents $C_{1-4}$ alkyl;

m and n independently represents 0, 1 or 2;

or a pharmaceutically acceptable salt thereof.

In another embodiment when $R^1$ represents -heteroaryl, -heteroaryl-X-aryl, -heteroaryl-X-heteroaryl or -heteroaryl-X-heterocyclyl, the heteroaryl group attached directly to the piperidine is other than benzoxazol-2-yl.

In a further embodiment, in which $R^2$ represent $C_{1-6}$ alkyl or $C_{3-6}$ cycloalkyl, $R^1$ is other than pyrimidin-4-yl.

In yet another embodiment in which $R^1$ represents -heteroaryl, $R^2$ does not represent -methyl-$C_{3-6}$ cycloalkyl.

DETAILED DESCRIPTION

The term '$C_{1-6}$ alkyl' as used herein as a group or a part of the group refers to a linear or branched saturated hydrocarbon group containing from 1 to 6 carbon atoms. Examples of such groups include methyl, ethyl, n-propyl, isopropyl, n-butyl, isobutyl, sec-butyl, tert butyl, n-pentyl, isopentyl, neopentyl or hexyl and the like.

The term '$C_{2-6}$ alkenyl' as used herein refers to a linear or branched hydrocarbon group containing one or more carbon-carbon double bonds and having from 2 to 6 carbon atoms. Examples of such groups include ethenyl, propenyl, butenyl, pentenyl or hexenyl and the like.

The term '$C_{1-6}$ alkoxy' as used herein refers to an —O—$C_{1-6}$ alkyl group wherein $C_{1-6}$ alkyl is as defined herein. Examples of such groups include methoxy, ethoxy, propoxy, butoxy, pentoxy or hexoxy and the like.

The term '$C_{3-8}$ cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term 'halogen' as used herein refers to a fluorine, chlorine, bromine or iodine atom.

The term 'halo$C_{1-6}$ alkyl' as used herein refers to a $C_{1-6}$ alkyl group as defined herein wherein one hydrogen atom is replaced with halogen. An example of such a group includes fluoroethyl. The term 'polyhalo$C_{1-6}$ alkyl' as used herein refers to a $C_{1-6}$ alkyl group as defined herein wherein at least two hydrogen atoms are replaced with halogen. Examples such groups include trifluoromethyl or trifluoroethyl and the like.

The term 'halo $C_{1-6}$ alkoxy' as used herein refers to a $C_{1-6}$ alkoxy group as herein defined wherein one hydrogen atom is replaced with halogen. An examples of such a group includes fluoromethoxy. The term 'polyhalo$C_{1-6}$ alkoxy' as used herein refers to a $C_{1-6}$ alkoxy group as defined herein wherein at least two hydrogen atoms are replaced with halogen. Examples such groups include difluoromethoxy or trifluoromethoxy and the like.

The term '$C_{1-6}$ alkylamido$C_{1-6}$ alkyl' as used herein encompasses the group —$C_{1-6}$ alkyl-CONH—$C_{1-6}$ alkyl, and the group —$C_{1-6}$ alkyl-NHCO—$C_{1-6}$ alkyl.

The term 'aryl' as used herein refers to a $C_{6-12}$ monocyclic or bicyclic hydrocarbon ring wherein at least one ring is aromatic. Examples of such groups include phenyl, naphthyl or tetrahydronaphthalenyl and the like.

The term 'aryloxy' as used herein refers to an —O-aryl group wherein aryl is as defined herein. Examples of such groups include phenoxy and the like.

The term 'heteroaryl' as used herein refers to a 5-6 membered monocyclic aromatic or a fused 8-10 membered bicyclic aromatic ring, which monocyclic or bicyclic ring contains 1 to 4 heteroatoms selected from oxygen, nitrogen and sulphur. Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazinyl, tetrazinyl and the like. Examples of such fused aromatic rings include quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridinyl, furopyridinyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and the like.

The term 'heterocyclyl' refers to a 4-7 membered monocyclic ring or a fused 8-12 membered bicyclic ring which may be saturated or partially unsaturated, which monocyclic or bicyclic ring contains 1 to 4 heteroatoms selected from oxygen, nitrogen or sulphur. Examples of such monocyclic rings include pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridinyl, tetrahydropyrimidinyl, tetrahydrothiophenyl, tetrahydrothiopyranyl, diazepanyl, azepanyl and the like. Examples of such bicyclic rings include indolinyl, isoindolinyl, benzopyranyl, quinuclidinyl, 2,3,4,5-tetrahydro-1H-3-benzazepine, tetrahydroisoquinolinyl and the like.

In one embodiment, $R^1$ represents -aryl, -heteroaryl, -aryl-X-heteroaryl or heteroaryl-X-heteroaryl.

In one embodiment in which $R^1$ represents -aryl-X-heteroaryl or -heteroaryl-X-heteroaryl and the aryl or heteroaryl linked to the nitrogen atom of the piperidine group is a 6 membered ring, the bond to X is in the para position relative to the attachment to the linkage to the nitrogen atom of the piperidine group.

In one aspect, the aryl or heteroaryl groups of $R^1$ may optionally be substituted by one or more (e.g. 1, 2 or 3) substituents which may be the same or different, and which are selected from the group consisting of halogen, cyano, $C_{1-6}$ alkyl, polyhalo$C_{1-6}$ alkyl, or a group —COR$^{15}$, —COOR$^{15}$ or —CONR$^{15}$R$^{16}$, wherein R$^{15}$ and R$^{16}$ independently represent, hydrogen, $C_{1-6}$ alkyl (e.g. methyl, ethyl, isopropyl or tert-butyl) or polyhalo$C_{1-6}$ alkyl (e.g. trifluoromethyl).

In one embodiment in which $R^1$ represents -aryl or-heteroaryl, wherein the aryl and heteroaryl groups are six membered rings that are substituted by one substituent, the substituent is in the para position relative to the attachment to X.

In a more particular embodiment, $R^1$ represents:
- aryl (e.g. phenyl) optionally substituted by a —COR$^{15}$ (e.g. —COMe or —COCF$_3$) or halogen (e.g. fluorine) group;

-heteroaryl (e.g. pyrid-2-yl, pyrid-3-yl, pyrid-4-yl, pyrazin-2-yl, pyridazin-3-yl, pyrimidin-5-yl or quinolin-6-yl) optionally substituted by a cyano, $C_{1-6}$ alkyl (e.g. methyl), polyhalo$C_{1-6}$ alkyl (e.g. —$CF_3$), —$CONR^{15}R^{16}$ (e.g. —CON(H)(Me), —CON(H)(Et), —CON(H)(i-Pr), —$COR^{15}$ (e.g. —COMe) or —$COOR^{15}$ (e.g. —COOt—Bu) group;

-aryl-X-heteroaryl (e.g.-phenyl-oxadiazolyl) optionally substituted by a halogen (e.g. fluorine) or $C_{1-6}$ alkyl (e.g. methyl); or -heteroaryl-X-heteroaryl (e.g. -pyridyl-oxadiazolyl) optionally substituted by a $C_{1-6}$ alkyl (e.g. methyl) group.

More particularly, $R^1$ represents:

-aryl (e.g. phenyl) optionally substituted by a —$COR^{15}$ (e.g. —COMe or —$COCF_3$);

-heteroaryl (e.g. pyrid-2-yl, pyrid-3-yl, pyrazin-2-yl, pyridazin-3-yl or pyrimidin-5-yl) optionally substituted by a cyano, polyhalo$C_{1-6}$ alkyl (e.g. —$CF_3$), —$CONR^{15}R^{16}$ (e.g. —CON(H)(Me), —CON(H)(Et), —CON(H)(i-Pr), —$COR^{15}$ (e.g. —COMe) or —$COOR^{15}$ (e.g. —COOH, —COOMe or —COOt—Bu) group;

-aryl-X-heteroaryl (e.g.-phenyl-1,2,4-oxadiazol-5-yl), wherein the aryl group is optionally substituted by a halogen (e.g. fluorine), and wherein the heteroaryl group is optionally substituted by $C_{1-6}$ alkyl (e.g. methyl); or -heteroaryl-X-heteroaryl (e.g. -pyrid-3-yl-1,2,4-oxadiazol-5-yl) optionally substituted on the terminal heteroaryl group by a $C_{1-6}$ alkyl (e.g. methyl) group.

Even more particularly, $R^1$ represents

-heteroaryl (e.g. pyrid-3-yl or pyrazin-2-yl) optionally substituted by a cyano, —$CONR^{15}R^{16}$ (e.g. —CON(H)(Me), —CON(H)(Et) or —CON(H)(i-Pr)) or —$COR^{15}$ (e.g. —COMe) group; or -aryl-X-heteroaryl (e.g. -phenyl-1,2,4-oxadiazol-5-yl) optionally substituted on the aryl group by a halogen (e.g. fluorine), and optionally substituted on the heteroaryl group by a $C_{1-6}$ alkyl (e.g. methyl) group); or -heteroaryl-X-heteroaryl (e.g. -pyrid-3-yl-1,2,4-oxadiazol-5-yl) optionally substituted on the terminal heteroaryl group by a $C_{1-6}$ alkyl (e.g. methyl) group.

Most particularly, $R^1$ represents

-pyrazin-2-yl or pyrid-3-yl optionally substituted by —$CONR^{15}R^{16}$ (e.g. —CON(H)(Me), —CON(H)(Et) or —CON(H)(i-Pr)) or —$COR^{15}$ (e.g. —COMe) group;

-pyrid-3-yl-1,2,4-oxadiazol-5-yl optionally substituted on the oxadiazolyl group by a $C_{1-6}$ alkyl (e.g. methyl) group; or -phenyl-1,2,4-oxadiazol-5-yl optionally substituted on the phenyl group by a halogen (e.g. fluorine) and optionally substituted on the oxadiazolyl group by a $C_{1-6}$ alkyl (e.g. methyl) group.

In another embodiment, X represents a bond.

In a further embodiment, $R^2$ represents $C_{1-8}$ alkyl (e.g. methyl, ethyl or isopropyl), $C_{3-6}$ cycloalkyl (e.g. cyclobutyl), $C_{1-4}$alkyl-$C_{3-6}$cycloalkyl (e.g. cyclopropylmethyl).

In a more particular embodiment, $R^2$ represents isopropyl or cyclobutyl, particularly cyclobutyl.

In one embodiment, m and n both represent 0.

In one aspect, the invention provides a compound of formula (I) or a pharmaceutically acceptable salt thereof, wherein:

$R^1$ represents aryl, heteroaryl, -aryl-X-heteroaryl, or -heteroaryl-X-heteroaryl; wherein said aryl, heteroaryl and heterocyclyl groups of $R^1$ may optionally be substituted by one or more (e.g. 1, 2 or 3) substituents which may be the same or different, and which are selected from the group consisting of halogen, cyano, $C_{1-6}$ alkyl, polyhalo$C_{1-6}$ alkyl, or a group —$COR^{15}$, —$COOR^{15}$ or —$CONR^{15}R^{16}$;

X represents a bond;

$R^2$ represents $C_{1-8}$ alkyl, $C_{3-6}$ cycloalkyl or —$C_{1-4}$alkyl-$C_{3-6}$ cycloalkyl;

m and n represent 0;

or solvates thereof.

Compounds according to the invention include examples E1-E36 as shown below, or a pharmaceutically acceptable salt or solvate thereof.

More particularly, compounds according to the invention include:

5-{4-[(1-Cyclobutyl-4-piperidinyl)methyl]-1-piperidinyl}-N-(1-methylethyl)-2-pyrazinecarboxamide (E6);

5-{4-[(1-cyclobutyl-4-piperidinyl)methyl]-1-piperidinyl}-N-ethyl-2-pyrazinecarboxamide (E9);

5-(4-{[1-(1-Methylethyl)-4-piperidinyl]methyl}-1-piperidinyl)-2-(3-methyl-1,2,4-oxadiazol-5-yl)pyridine (E15);

1-[3-fluoro-4-(3-methyl-1,2,4-oxadiazol-5-yl)phenyl]-4-{[1-(1-methylethyl)-4-piperidinyl]methyl}piperidine (E16);

5-{4-[(1-cyclobutyl-4-piperidinyl)methyl]-1-piperidinyl}-2-(3-methyl-1,2,4-oxadiazol-5-yl)pyridine (E17);

1-[5-(4-{[1-(1-Methylethyl)-4-piperidinyl]methyl}-1-piperidinyl)-2-pyridinyl]ethanone (E23); and 1-(5-{4-[(1-Cyclobutyl-4-piperidinyl)methyl]-1-piperidinyl}-2-pyridinyl)ethanone (E24);

and pharmaceutically acceptable salts and solvates thereof.

Most particularly, compounds according to the invention include:

5-{4-[(1-Cyclobutyl-4-piperidinyl)methyl]-1-piperidinyl}-N-(1-methylethyl)-2-pyrazinecarboxamide (E6); and 5-(4-{[1-(1-Methylethyl)-4-piperidinyl]methyl}-1-piperidinyl)-2-(3-methyl-1,2,4-oxadiazol-5-yl)pyridine (E15);

and pharmaceutically acceptable salts and solvates thereof.

A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

The invention includes within its scope all possible stoichiometric and non-stoichiometric forms of the salts of the compounds of formula (I) including hydrates and solvates.

Certain compounds of formula (I) are capable of existing in stereoisomeric forms. It will be understood that the invention encompasses all geometric and optical isomers of these compounds and the mixtures thereof including racemates. Tautomers also form an aspect of the invention.

The present invention also provides a process for the preparation of a compound of formula (I) or a pharmaceutically acceptable salt thereof, which process comprises:
(a) reacting a compound of formula (II)

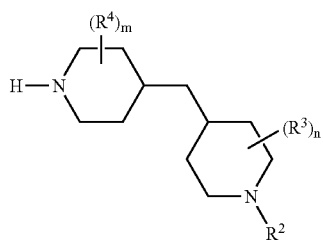

wherein $R^2$, $R^3$, $R^4$, m and n are as defined above, with a compound of formula $R^1\text{-}L^1$, wherein $R^1$ is as defined above and $L^1$ represents a suitable leaving group, such as a halogen atom (e.g. fluorine, chlorine, bromine or iodine); or
(b) deprotecting a compound of formula (I) or converting groups which are protected; and optionally thereafter
(c) interconversion from one compound of formula (I) to another.

Process (a) typically comprises the use of a suitable base, such as potassium carbonate in a suitable solvent such as dimethylsulfoxide, 1-methyl-2-pyrrolidinone, N,N-dimethylformamide or acetonitrile at elevated temperature. Alternatively, process (a) may be carried out with a suitable catalyst system in the presence of a suitable base such as sodium t-butoxide, caesium carbonate or potassium phosphate in a solvent such as o-xylene, dioxane or toluene, under an inert atmosphere, optionally at an elevated temperature. Suitable catalyst systems include tris(dibenzylideneacetone)dipalladium(0) and 2-dicyclohexylphosphino-2'-(N,N-dimethylamino)biphenyl, bis(dibenzylideneacetone)palladium and 2-dicyclohexylphosphino-2'-(N,N-dimethylamino)biphenyl, tris(dibenzylideneacetone)dipalladium(0) and xantphos, acetato(2'-di-t-butylphosphino-1,1'-biphenyl-2-yl)palladium (II), palladium(II) acetate and BINAP, or palladium(II) acetate and 2,8,9-triisobutyl-2,5,8,9-tetraaza-1-phosphabicyclo[3.3.3]undecane.

In process (b), examples of protecting groups and the means for their removal can be found in T. W. Greene 'Protective Groups in Organic Synthesis' (J. Wiley and Sons, 1991). Suitable amine protecting groups include sulfonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid.

Process (c) may be performed using conventional interconversion procedures such as epimerisation, oxidation, reduction, alkylation, nucleophilic or electrophilic aromatic substitution, ester hydrolysis or amide bond formation. Examples of transition metal mediated coupling reactions useful as interconversion procedures include the following: Palladium catalysed coupling reactions between organic electrophiles, such as aryl halides, and organometallic reagents, for example boronic acids (Suzuki cross-coupling reactions); Palladium catalysed amination and amidation reactions between organic electrophiles, such as aryl halides, and nucleophiles, such as amines and amides; Copper catalysed amidation reactions between organic electrophiles (such as aryl halides) and nucleophiles such as amides; and Copper mediated coupling reactions between phenols and boronic acids.

Compounds of formula (II) may be prepared in accordance with the following procedure:

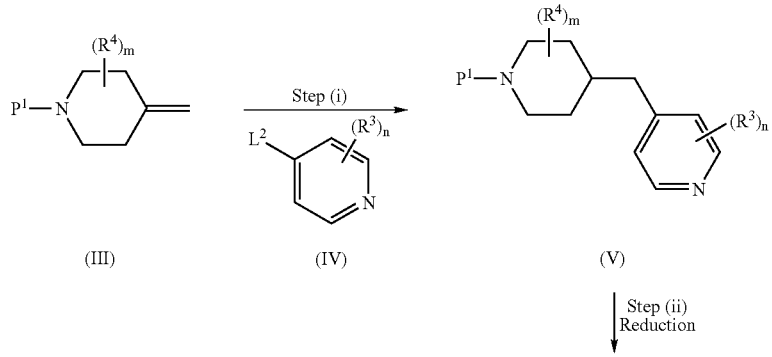

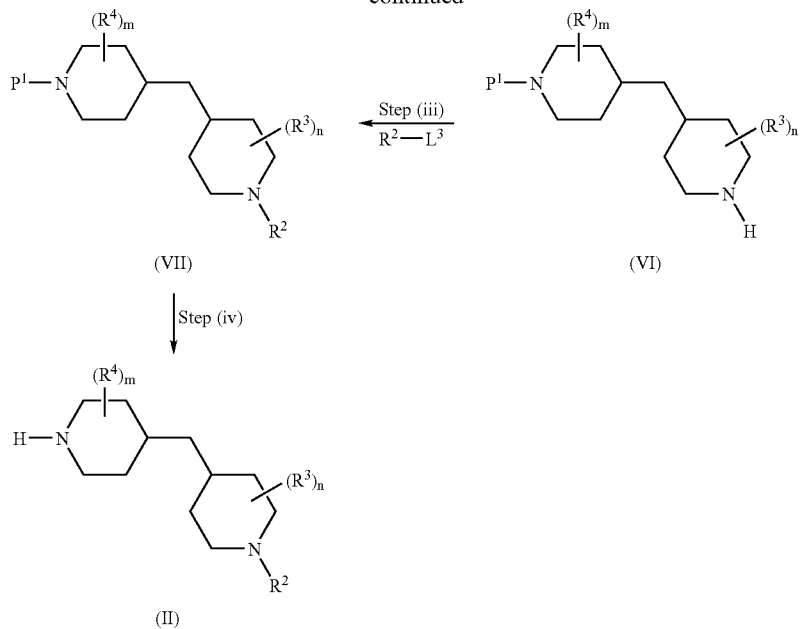

wherein $R^2$, $R^3$, $R^4$, m and n are as defined above, $L^2$ represents a suitable leaving group such as a halogen atom (e.g. bromine), and $P^1$ represents a suitable protecting group such as t-butoxycarbonyl.

Step (i) comprises the use of a borane such as 9-borabicyclo[3.3.1]nonane in a solvent such as tetrahydrofuran, followed by treatment with a suitable palladium catalyst such as [1,1'-bis(diphenylphosphino)ferrocene]dichloropalladium (II), complex with dichloromethane (1:1), in the presence of a base such as potassium carbonate in a suitable solvent such as N,N-dimethylformamide, at elevated temperature.

Step (ii) is carried out under reductive conditions using hydrogen gas with a platinum catalyst in a solvent such as ethanol at a suitable temperature such as room temperature.

Step (iii) may be performed by reacting a compound of formula (VI) with a compound of formula $R^2$-$L^3$ wherein $R^2$ is as defined above and $L^3$ represents a suitable leaving group such as a halogen atom or a sulfonate. Where $L^3$ represents halogen (e.g. iodine) or a sulfonate (e.g. methylsulfonate), step (iii) typically comprises the use of a suitable base such as potassium carbonate in a solvent such as acetonitrile optionally at elevated temperature.

Step (iii) may also be performed by reacting a compound of formula (VI) with a compound of formula $R^{2'}C=O$, capable of converting an NH group to an $NR^2$ group. Step (iii) typically takes place under reductive conditions e.g. using sodium triacetoxyborohydride and a suitable base such as triethylamine, in a solvent such as DCM.

Step (iv) is a deprotection reaction where the conditions depend on the nature of the group $P^1$. Process (b) describes processes for removing protecting groups. Removal of a $P^1$ tert-butoxycarbonyl group can be performed under acidic conditions e.g. using 4 N HCl in a suitable solvent such as dioxane.

Compounds of formula (III), (IV), $R^1$-$L^1$, $R^2$-$L^3$ and $R^{2'}C=O$ are either known in the literature or can be prepared by analogous methods.

Compounds of formula (I) and their pharmaceutically acceptable salts have affinity for and are antagonists and/or inverse agonists of the histamine H3 receptor and are believed to be of potential use in the treatment of neurological diseases including Alzheimer's disease, dementia (including Lewy body dementia and vascular dementia), age-related memory dysfunction, mild cognitive impairment, cognitive deficit, epilepsy, pain of neuropathic origin including neuralgias, neuritis and back pain, and inflammatory pain including osteoarthritis, rheumatoid arthritis, acute inflammatory pain and back pain, migraine, Parkinson's disease, multiple sclerosis, stroke and sleep disorders (including narcolepsy and sleep deficits associated with Parkinson's disease); psychiatric disorders including schizophrenia (particularly cognitive deficit of schizophrenia), attention deficit hyperactivity disorder, depression, anxiety and addiction; and other diseases including obesity and gastro-intestinal disorders.

It will also be appreciated that compounds of formula (I) are expected to be selective for the histamine H3 receptor over other histamine receptor subtypes, such as the histamine H1 receptor. Generally, compounds of the invention may be at least 10 fold selective for H3 over H1, such as at least 100 fold selective.

Thus the invention also provides a compound of formula (I) or a pharmaceutically acceptable salt thereof, for use as a therapeutic substance in the treatment or prophylaxis of the above disorders, in particular cognitive impairments in diseases such as Alzheimer's disease and related neurodegenerative disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment of the above disorders.

When used in therapy, the compounds of formula (I) are usually formulated in a standard pharmaceutical composition. Such compositions can be prepared using standard procedures.

Thus, the present invention further provides a pharmaceutical composition for use in the treatment of the above disorders which comprises the compound of formula (I) or a pharmaceutically acceptable salt thereof and a pharmaceutically acceptable carrier.

The present invention further provides a pharmaceutical composition which comprises the compound of formula (I) or a pharmaceutically acceptable salt thereof and a pharmaceutically acceptable carrier.

Compounds of formula (I) may be used in combination with other therapeutic agents, for example medicaments claimed to be useful as either disease modifying or symptomatic treatments of Alzheimer's disease. Suitable examples of such other therapeutic agents may be agents known to modify cholinergic transmission such as 5-$HT_6$ antagonists, M1 muscarinic agonists, M2 muscarinic antagonists or acetylcholinesterase inhibitors. When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.1 to 200 mg and even more suitably 1.0 to 200 mg, and such unit doses may be administered more than once a day, for example two or three a day. Such therapy may extend for a number of weeks or months.

The following Descriptions and Examples illustrate the preparation of compounds of the invention. An Emrys™ Optimizer microwave reactor was employed for reactions carried out with microwave heating. Where indicated, Varian Mega BE (10 g) SCX columns or Isolute Flash SCX-2 (20 g) columns were used for the work-up of reactions. Crude mixtures were applied to the column, non-polar materials were washed off with methanol, and the desired amines were eluted with ammonia in methanol.

Description 1

1,1-Dimethylethyl
4-(4-pyridinylmethyl)-1-piperidinecarboxylate (D1)

9-borabicyclo[3.3.1]nonane (101.5 ml of a 0.5M solution in tetrahydrofuran) was added to a degassed sample of N-(tert-butoxycarbonyl)-4-methylene piperidine (may be prepared as described in A. Palani et al., J. Med. Chem., 2002, 45: 3145) (10 g) and the resultant solution heated at reflux for 1 h. After cooling to room temperature the reaction mixture was then added to a mixture of 4-bromopyridine (7.23 g), [1,1'-bis(diphenylphosphino)ferrocene]dichloropalladium (II), complex with dichloromethane (1:1) (1.14 g), $K_2CO_3$ (8.42 g), N,N-dimethylformamide (100 ml) and water (10 ml), and the resultant mixture heated at 60° C. for 3 h. After cooling to room temperature, another charge of [1,1'-bis(diphenylphosphino)ferrocene]dichloropalladium(II), complex with dichloromethane (1:1) (1.14 g) was added to the reaction and heated at 60° C. overnight. The mixture was cooled to room temperature and poured into water, the pH was adjusted to 11 by the addition of 10% aqueous sodium hydroxide and extracted into ethyl acetate. Combined organic extracts were dried ($Na_2SO_4$) and evaporated to give the crude pyridine as a brown viscous oil. Chromatography

[silica gel, eluting with ethyl acetate in hexanes, 0-100%] gave the title compound (D1) as a pale yellow oil (7.5 g).

Description 2

1,1-Dimethylethyl 4-(4-piperidinylmethyl)-1-piperidinecarboxylate (D2)

1,1-Dimethylethyl 4-(4-pyridinylmethyl)-1-piperidinecarboxylate (may be prepared as described in Description 1) (11.4 g) was dissolved in ethanol (200 ml) and acetic acid (2.36 ml). Platinum oxide (2 g) was added under a blanket of argon, and the reaction shaken under hydrogen at 50 psi for 18 h. After carefully filtering off the platinum catalyst, the solvent was evaporated and the residue redissolved in ethyl acetate (50 ml) and washed with saturated sodium hydrogen carbonate solution (50 ml). The aqueous phase was extracted into ethyl acetate (2×50 ml) and the combined organics dried ($Na_2SO_4$) and evaporated to give the title compound (D2) as white solid (9.4 g).

Description 3

1,1-Dimethylethyl 4-{[1-(1-methylethyl)-4-piperidinyl]methyl}-1-piperidinecarboxylate (D3)

1,1-Dimethylethyl 4-(4-piperidinylmethyl)-1-piperidinecarboxylate (may be prepared as described in Description 2) (3 g), isopropyl iodide (3.2 ml) and $K_2CO_3$ (2.94 g) were combined in acetonitrile (70 ml) and the reaction mixture heated at 50° C. overnight. The reaction was allowed to cool to room temperature, filtered and evaporated. The residue was dissolved in diethylether (50 ml) and washed successively with water (50 ml), saturated sodium thiosulphate solution (50 ml), saturated brine (50 ml) and dried ($Na_2SO_4$). The solvent was evaporated to give the title compound (D3) as a pale yellow oil (3.1 g).

Description 4

1-(1-Methylethyl)-4-(4-piperidinylmethyl)piperidine (D4)

1,1-Dimethylethyl 4-{[1-(1-methylethyl)-4-piperidinyl]methyl}-1-piperidinecarboxylate (may be prepared as described in Description 3) (3.1 g) was stirred in a solution of HCl-Dioxane (100 ml, 4M) for 2.5 h. The solvent was evaporated and the resultant yellow solid was dissolved in saturated potassium carbonate (25 ml). The solution was extracted into dichloromethane (3×50 ml) and the combined organics dried ($MgSO_4$) and evaporated to give the title compound (D4) as a pale yellow oil (1.8 g).

Description 5

1,1-Dimethylethyl 4-[(1-cyclobutyl-4-piperidinyl)methyl]-1-piperidinecarboxylate (D5)

1,1-Dimethylethyl 4-(4-piperidinylmethyl)-1-piperidinecarboxylate (may be prepared as described in Description 2) (4.8 g), cyclobutanone (3.81 ml) and triethylamine (4.7 ml) were stirred in DCM (200 ml) at room temperature. After 10 min sodium triacetoxyborohydride (7.2 g) was added and the reaction was stirred at room temperature overnight. The reaction mixture was evaporated and redissolved in dichloromethane (50 ml). After washing with saturated potassium carbonate solution (2×50 ml), saturated sodium hydrogen carbonate solution (2×50 ml) and saturated brine (50 ml) the organic phase was dried ($MgSO_4$) and evaporated to give the title compound (D5) as a colourless solid (5.72 g).

Description 6

1-Cyclobutyl-4-(4-piperidinylmethyl)piperidine (D6)

1,1-Dimethylethyl 4-[(1-cyclobutyl-4-piperidinyl)methyl]-1-piperidinecarboxylate (may be prepared as described in Description 5) (5.7 g) was stirred in a solution of HCl-Dioxane (100 ml, 4M) for 1 h. The solvent was evaporated and the resultant yellow solid was dissolved in saturated potassium carbonate (25 ml). The solution was extracted into dichloromethane (3×50 ml) and the combined organics dried ($MgSO_4$) and evaporated to give the title compound (D6) as a pale yellow oil which solidified on standing (3.04 g).

Description 7

1,1-Dimethylethyl 4-[(1-ethyl-4-piperidinyl)methyl]-1-piperidinecarboxylate (D7)

1,1-Dimethylethyl 4-(4-piperidinylmethyl)-1-piperidinecarboxylate (may be prepared as described in Description 2) (2 g), ethyl iodide (0.57 ml) and $K_2CO_3$ (1.96 g) were combined in acetonitrile (70 ml) and the reaction mixture was stirred at room temperature for 3 h. The reaction was filtered to remove solids and the solvent evaporated to give the title compound (D7) as a yellow solid (2.5 g).

Description 8

1-Ethyl-4-(4-piperidinylmethyl)piperidine (D8)

1,1-Dimethylethyl 4-[(1-ethyl-4-piperidinyl)methyl]-1-piperidinecarboxylate (may be prepared as described in Description 7) (2.5 g) was stirred in a solution of HCl-Dioxane (70 ml, 4M) for 2 h. The solvent was evaporated and the resultant hydrochloride salt was dissolved in saturated potassium carbonate (25 ml). The solution was extracted into DCM (3×50 ml) and the combined organics dried ($MgSO_4$) and evaporated to give the title compound (D8) (1.48 g).

Description 9

1,1-Dimethylethyl 4-{[1-(cyclopropylmethyl)-4-piperidinyl]methyl}-1-piperidinecarboxylate (D9)

1,1-Dimethylethyl 4-(4-piperidinylmethyl)-1-piperidinecarboxylate (may be prepared as described in Description 2) (2.0 g), cyclopropyl carboxaldehyde (1.6 ml) and triethylamine (1.99 ml) were stirred in dichloromethane (70 ml) at room temperature. After 10 min sodium triacetoxyborohydride (3.1 g) was added and the reaction was stirred at room temperature overnight. The reaction mixture was washed with saturated potassium carbonate solution (2×50 ml), saturated sodium hydrogen carbonate solution (2×50 ml) and saturated brine (50 ml). The organic phase was dried ($MgSO_4$) and evaporated to give the title compound (D9) (2.0 g).

Description 10

1-(Cyclopropylmethyl)-4-(4-piperidinylmethyl)piperidine (D10)

1,1-Dimethylethyl 4-{[1-(cyclopropylmethyl)-4-piperidinyl]methyl}-1-piperidinecarboxylate (may be prepared as described in Description 9) (2.0 g) was stirred in a solution of HCl-Dioxane (700 ml, 4M) for 2 h. The solvent was evaporated and the resultant yellow solid was dissolved in saturated potassium carbonate (25 ml). The solution was extracted into dichloromethane (3×50 ml) and the combined organics dried (MgSO$_4$) and evaporated to give the title compound (D10) (1.0 g).

Description 11

5-Bromo-2-pyridinecarboxylic acid (D11)

5-Bromo-2-cyanopyridine (95.0 g, 0.519 mol) was added portionwise with stirring over 2 min to concentrated hydrochloric acid (650 ml) at rt. The solution was stirred at rt for 25 min and then it was heated at 110° C. for 4.5 h under an atmosphere of argon. The solution was then allowed to cool to rt over 4 h and the resulting white crystals were filtered and washed with de-ionised water (4×200 ml). The solid was then suspended in toluene (500 ml) and the mixture evaporated to dryness. This was repeated with more toluene (500 ml) and the resulting white powder was dried under vacuum at 50° C. for 18 h to give the title compound (D11) (74.4 g). MS electrospray (−ve ion) 200 and 202 (M-H$^-$). $^1$H NMR δ (DMSO-d6): 13.40 (1H, br.s), 8.82 (1H, d, J=2.5 Hz), 8.25 (1H, dd, J=8, 2.5 Hz), 7.98 (1H, d, J=8 Hz).

Description 12

1,1-Dimethylethyl 5-bromo-2-pyridinecarboxylate (D12)

A suspension of 5-bromo-2-pyridinecarboxylic acid (may be prepared as described in Description 11) (68.0 g) in tert-butanol (680 ml) and pyridine (190 ml) was stirred vigorously at rt for 0.5 h under argon. 4-Toluenesulfonyl chloride (153.7 g) was then added portionwise over 10 min to give a thick white mixture which gradually dissolved over 2 h to give a dark brown solution. After 4.5 h at rt the reaction mixture was poured slowly with stirring onto a saturated aqueous solution of sodium hydrogen carbonate (136 g) in water (1 l). Stirring was continued for 18 h at rt. The product was then extracted into diethyl ether (2×1 l) and the combined extracts were dried (MgSO$_4$), filtered and concentrated to give a solid. This was treated with toluene (1 l) and the mixture was evaporated to dryness. This was repeated twice more with toluene (2×1 l) to give a pink solid which was dried in vacuo overnight to give 80.0 g of product. Recrystallisation from acetone/water gave the pure title compound (D12) (66.8 g). MS electrospray (+ve ion) 281 (MNa$^+$). $^1$H NMR δ CDCl$_3$: 8.79 (1H, s), 7.90 (2H, s), 1.64 (9H, s).

Description 13

4-Bromo-N-[(1-(dimethylamino)ethylidene]benzamide (D13)

4-Bromobenzamide (51.48 g) was heated in N,N-dimethylacetamide dimethylacetal (165 ml) at 120° C. for 2 h. The solution was allowed to cool overnight and the product crystallised as pale yellow needles, which were collected by filtration, washed on the filter with diethyl ether and dried overnight at 40° C. in vacuo to give the title compound (D13) (57.84 g). $^1$H NMR δ[DMSO-d6]: 2.26 (3H, s), 3.13 (3H, s), 3.14 (3H, s), 7.61 (2H, d, J=8.6 Hz), 7.94 (2H, d, J=8.6 Hz).

Description 14

5-(4-Bromophenyl)-3-methyl-1,2,4-oxadiazole (D14)

Method A

4-Bromo-N-[(1-(dimethylamino)ethylidene]benzamide (may be prepared as described in Description 13) (57.8 g) was treated with a solution of hydroxylamine hydrochloride (19.6 g) in 1M NaOH solution (350 ml). Dioxane (350 ml) and glacial acetic acid (450 ml) were added, and the resulting solution was stirred at 25° C. for 30 min and then at 90° C. for 3 h. After cooling overnight, the crystalline product (colourless needles) was collected by filtration, washed with dilute aqueous acetic acid and water and dried at 50° C. in vacuo to give the title compound (D14). Concentration of the filtrate yielded a second crop of product, spectroscopically identical to the first, which was collected and dried as before (46.1 g total). $^1$H NMR δ [CDCl$_3$]: 2.48 (3H, s), 7.67 (2H, d, J=8.4 Hz), 7.98 (2H, d, J=8.4 Hz); (MH)$^+$=239, 241.

Method B

4-Bromobenzamide (5.3 g) and N,N-dimethylacetamide dimethylacetal (35 ml) were heated together at 125° C. for 2 h. The reaction was allowed to cool to rt and the liquid evaporated to give a pale yellow solid. Hydroxylamine hydrochloride (2.2 g) in 1 N NaOH solution (36 ml) was added, followed by dioxane (36 ml) then AcOH (48 ml). The reaction mixture was stirred at rt for 30 min then heated at 90° C. for 3 h. The reaction was allowed to cool to rt and saturated aqueous K$_2$CO$_3$ solution (100 ml) was added followed by DCM (200 ml) before filtering. The organic phase was separated from the mixture, then saturated brine (100 ml) was added and the aqueous phase was extracted into EtOAc (200 ml). The combined organic phases were dried (Na$_2$SO$_4$) and evaporated to give a brown solid. The crude product was purified by column chromatography (silica gel, step gradient 10-50% EtOAc in hexanes) to give the title compound (D14) as a white solid (2.9 g). LCMS electrospray (+ve) 239, 241 (MH$^+$).

Description 15

5-(4-Bromo-3-fluorophenyl)-3-methyl-1,2,4-oxadiazole (D15)

4-Bromo-3-fluorobenzoic acid (10.09 g) was heated at reflux in thionyl chloride (100 ml) for 4 h and then allowed to cool. The mixture was evaporated in vacuo and the residue re-evaporated with dichloromethane (2×) to give the acid chloride as a light brown oil. This was added dropwise to vigorously stirred, ice-cooled concentrated aqueous ammonia (100 ml) and the precipitated product was collected by filtration, washed on the filter with water and dried at 40° C. in vacuo to give 4-bromo-3-fluorobenzamide as a white solid (9.13 g). This material and N,N-dimethylacetamide dimethylacetal (27 ml) were heated together at 120° C. for 2 h. The reaction was allowed to cool to rt and the liquid evaporated in vacuo to give a brown gum which was partitioned between saturated aqueous sodium hydrogen carbonate and ethyl acetate. The organic extract was washed with water and brine, dried and evaporated to give the acylamidine intermediate as a gum which solidified in vacuo, overnight (12.3 g). This intermediate was treated with a solution of hydroxylamine hydrochloride (4.16 g) in 1M aqueous sodium hydroxide (74.2 ml), dioxane (75 ml) and glacial acetic acid (95 ml). The reaction mixture was first stirred at rt for 30 min then heated at 90° C. for 3 h. On cooling a first crop of crystals was filtered off and dried in vacuo at 50° C. to give the title compound (D15) (5.5 g). The filtrate afforded a second crop of crystals (2.1 g). LCMS electrospray (+ve) 257 and 259 (MH$^+$).

Description 16

5-(4-Bromo-2-fluorophenyl)-3-methyl-1,2,4-oxadiazole (D16)

4-Bromo-2-fluorobenzoic acid (5.27 g) was heated at reflux in thionyl chloride (50 ml) for 4 h and then allowed to cool. The mixture was evaporated in vacuo and the residue re-evaporated with dichloromethane (2×) to give the acid chloride as a light brown oil. This was added dropwise to vigorously stirred, ice-cooled concentrated aqueous ammonia (50 ml) and when addition was complete the mixture was stirred for 5 min and then extracted with ethyl acetate (3×). The combined organic extracts were washed with water and brine, dried (Na$_2$SO$_4$) and evaporated to give 4-bromo-2-fluorobenzamide as a white solid (4.72 g). This material and N,N-dimethylacetamide dimethylacetal (17 ml) were heated together at 120° C. for 2 h. The reaction was allowed to cool to rt and the liquid evaporated in vacuo to give a brown gum which was partitioned between saturated aqueous sodium hydrogen carbonate and ethyl acetate. The organic extract was washed with water and brine, dried (Na$_2$SO$_4$) and evaporated to a gum. This was purified by chromatography (silica gel, eluant hexane/ethyl acetate) to give the acylamidine intermediate as a gum which solidified in vacuo (4.15 g). Hydroxylamine hydrochloride (1.32 g) in 1 N sodium hydroxide solution (23.5 ml) was added, followed by dioxane (23.5 ml) then acetic acid (30 ml). The reaction mixture was stirred at rt for 30 min then heated at 90° C. for 3 h. The reaction was allowed to cool to rt and poured into water. The pH was adjusted to ~9 by addition of solid NaHCO$_3$ and the precipitated product was collected by filtration, washed on the filter with water and dried at 40° C. in vacuo to give the title compound (D16) as a greyish-brown solid (2.82 g). LCMS electrospray (+ve) 257 and 259 (MH$^+$).

Description 17

5-Bromo-2-(3-methyl-1,2,4-oxadiazol-5-yl)pyridine (D17)

A suspension of 5-bromo-2-pyridinecarboxylic acid (may be prepared as described in Description 11) (4.5 g) and carbonyl diimidazole (3.97 g) in tetrahydrofuran was heated at reflux for 1.5 h. The reaction mixture was allowed to cool to room temperature, followed by evaporation of the tetrahydrofuran and replacing it with toluene (40 ml) as solvent. Acetamidoxime (4.95 g) was added and the reaction mixture heated at 80° C. for 18 h. The mixture was allowed to cool and diluted with ethyl acetate (60 ml) before washing sequentially with water (2×50 ml), 2 N sodium hydroxide (2×50 ml), water (2×50 ml) and saturated brine (2×50 ml). The organic phase was dried (Na$_2$SO$_4$) and evaporated to give the crude oxadiazole, which was recrystallised from hot ethanol/methanol to afford the title compound (D17) as colourless crystals (3.4 g). LCMS electrospray (+ve) 240 and 242 (MH$^+$).

Description 18

1,1-Dimethylethyl 4-[(1-methyl-4-piperidinyl)methyl]-1-piperidinecarboxylate (D18)

1,1-Dimethylethyl 4-(4-piperidinylmethyl)-1-piperidinecarboxylate (may be prepared as described in Description 2) (1.5 g), and LiAlH$_4$ (26.6 ml of 1M solution in tetrahydrofuran) were combined in tetrahydrofuran (10 ml) and the reaction mixture stirred at room temperature for 10 min before cooling to 0° C. in an ice/water bath. Ethyl formate (5 ml) was then added dropwise. The reaction was then quenched with 3 N sodium hydroxide solution. The solid precipitate formed was filtered and washed with more tetrahydrofuran. The combined organics were dried over Na$_2$SO$_4$, and evaporated to give the title compound (D18) (1.1 g).

Description 19

1-Methyl-4-(4-piperidinylmethyl)piperidine (D19)

1,1-Dimethylethyl 4-{[1-(1-methylethyl)-4-piperidinyl]methyl}-1-piperidinecarboxylate (may be prepared as described in Description 3) (3.1 g) was stirred in a solution of HCl-Dioxane (50 ml, 4M) for 2 h. The solvent was evaporated and the product was dissolved in saturated potassium carbonate (25 ml). The solution was extracted into dichloromethane (3×50 ml) and the combined organics dried (Na$_2$SO$_4$) and evaporated to give the title compound (D19) (0.658 g).

EXAMPLE 1

Methyl 5-{4-[(1-cyclobutyl-4-piperidinyl)methyl]-1-piperidinyl}-2-pyrazinecarboxylate (E1)

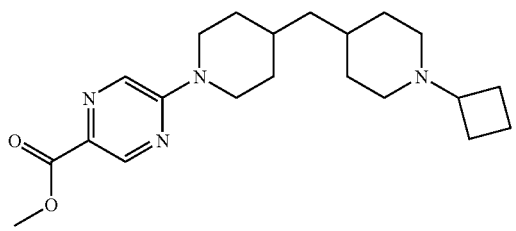

1-Cyclobutyl-4-(4-piperidinylmethyl)piperidine (may be prepared as described in Description 6) (0.59 g), methyl 5-chloro-2-pyrazinecarboxylate (0.43 g) and potassium carbonate (0.69 g) were dissolved in acetonitrile (5 ml) and heated at 120° C. for 10 min in the microwave reactor, followed by a further 15 min. The crude mixture was passed through an SCX column (10 g, eluting with methanol [80 ml] then 2 N NH$_3$ in methanol [80 ml]). The basic fractions were evaporated to give the title compound (E1) as a yellow solid (0.665 g). MS electrospray (+ion) 373 (MH$^+$)

EXAMPLE 2

Methyl 5-(4-{[1-(1-methylethyl)-4-piperidinyl]methyl}-1-piperidinyl)-2-pyrazinecarboxylate (E2)

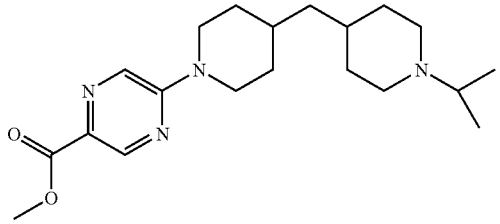

1-(1-Methylethyl)-4-(4-piperidinylmethyl)piperidine (may be prepared as described in Description 4) (0.50 g), methyl 5-chloro-2-pyrazinecarboxylate (0.575 g) and potassium carbonate (0.615 g) were dissolved in acetonitrile (5 ml) and heated at 120° C. for 5 min in the microwave reactor. The crude mixture was passed through an SCX column (10 g, eluting with methanol [80 ml] then 2 N $NH_3$ in methanol [80 ml]). The basic fractions were evaporated to give the title compound (E2) as a yellow crystalline solid (0.825 g). MS electrospray (+ion) 361 ($MH^+$)

EXAMPLE 3

1,1-Dimethylethyl 5-{4-[(1-cyclobutyl-4-piperidinyl)methyl]-1-piperidinyl}-2-pyridinecarboxylate (E3)

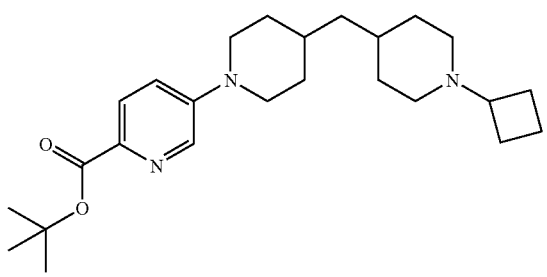

1-Cyclobutyl-4-(4-piperidinylmethyl)piperidine (may be prepared as described in Description 6) (0.50 g), 1,1-dimethylethyl 5-bromo-2-pyridinecarboxylate (may be prepared as described in Description 12) (0.66 g), BINAP (0.15 g) and $Cs_2CO_3$ (1.6 g) were added to toluene (20 ml) under argon and the reaction mixture degassed by sequential freezing in dry ice followed by warming to room temp under vacuum (3×). After stirring for 5 min Pd(OAc)$_2$ (0.05 g) was added and the reaction mixture heated at 80° C. for 20 h. The reaction mixture was filtered and evaporated, after which chromatography (silica gel, eluting with methanol/dichloromethane, 0-20%) afforded the title compound (E3) as a solid (0.23 g). MS electrospray (+ion) 414 ($MH^+$)

EXAMPLE 4

1,1-Dimethylethyl 5-(4-{[1-(1-methylethyl)-4-piperidinyl]methyl}-1-piperidinyl)-2-pyridinecarboxylate (E4)

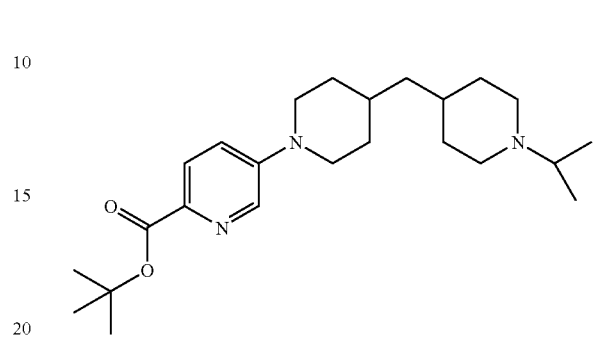

1-(1-Methylethyl)-4-(4-piperidinylmethyl)piperidine (may be prepared as described in Description 4) (0.25 g), 1,1-dimethylethyl 5-bromo-2-pyridinecarboxylate (may be prepared as described in Description 12) (0.29 g), BINAP (0.06 g) and $Cs_2CO_3$ (1.82 g) were added to toluene (50 ml) under argon and the reaction mixture degassed by sequential freezing in dry ice followed by warming to room temp under vacuum (3×). After stirring for 5 min Pd(OAc)$_2$ (0.05 g) was added, degassed again, and the reaction mixture heated at 100° C. for 24 h. The reaction mixture was filtered and evaporated, after which chromatography (silica gel, eluting with methanol/dichloromethane, 0-20%) afforded the title compound (E4) as a yellow solid (0.25 g). MS electrospray (+ion) 424 ($MNa^+$)

EXAMPLE 5

5-{4-[(1-Cyclobutyl-4-piperidinyl)methyl]-1-piperidinyl}-2-pyrazinecarboxylic acid hydrochloride (E5)

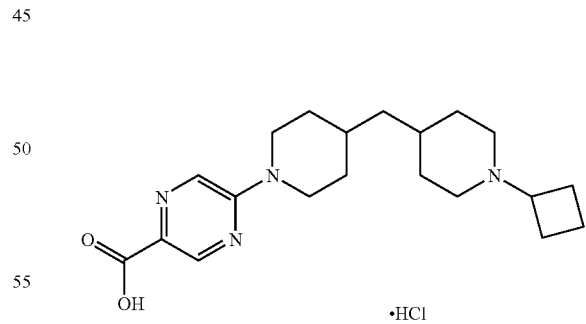

Methyl 5-{4-[(1-cyclobutyl-4-piperidinyl)methyl]-1-piperidinyl}-2-pyrazinecarboxylate (may be prepared as described in Example 1) (0.665 g) was dissolved in conc. HCl and heated at reflux for 1.5 h. The reaction mixture was evaporated, then re-evaporated from toluene (3×10 ml) to afford the crude acid hydrochloride salt (E5) as a yellow solid (0.705 g). MS electrospray (+ion) 359 ($MH^+$)

EXAMPLE 6

5-{4-[(1-Cyclobutyl-4-piperidinyl)methyl]-1-piperidinyl}-N-(1-methylethyl)-2-pyrazinecarboxamide (E6)

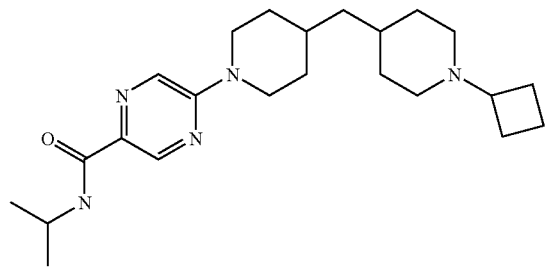

Step 1: 5-{4-[(1-cyclobutyl-4-piperidinyl)methyl]-1-piperidinyl}-2-pyrazinecarbonyl chloride 5-{4-[(1-Cyclobutyl-4-piperidinyl)methyl]-1-piperidinyl}-2-pyrazinecarboxylic acid hydrochloride (may be prepared as described in Example 5) (0.7 g) was dissolved in dichloromethane (50 ml) with oxalyl chloride (0.64 ml) and dimethylformamide (0.001 ml). After 1 h the reaction mixture was evaporated and the resultant yellow foam re-evaporated from dichloromethane (3×20 ml) to give the crude acid chloride, which was used in the next step immediately.

Step 2: 5-{4-[(1-Cyclobutyl-4-piperidinyl)methyl]-1-piperidinyl}-N-(1-methylethyl)-2-pyrazinecarboxamide 5-{4-[(1-Cyclobutyl-4-piperidinyl)methyl]-1-piperidinyl}-2-pyrazinecarbonyl chloride (0.67 g) was dissolved in dichloromethane (20 ml) and added dropwise to a stirred solution of isopropylamine (1.53 ml) in dichloromethane (10 ml) over 1 h. The reaction was allowed to stir for a further 15 h before the mixture was evaporated. Chromatography (silica gel, eluting with [2N NH$_3$ in methanol]/dichloromethane, 0-10%) afforded the carboxamide, which was recrystallised from ethyl acetate/ethanol to give the title compound (E6) (0.2 g). MS electrospray (+ion) 400 (MH$^+$).[1] H NMR δ (CDCl$_3$): 8.82 (1H, d, J=1.2 Hz), 7.93 (1H, d, J=1.2 Hz), 7.28 (1H, d, J=9.6 Hz), 4.42 (2H, d, J=13.2 Hz), 4.25 (1H, m), 2.90 (2H, m) 2.69 (1H, m), 2.10-1.81 (5H, m), 1.80-1.60 (8H, m, obscured by H$_2$O), 1.44-1.32 (4H, m), 1.31-1.14 (11H, m).

EXAMPLES 7-9 (E7-E9)

Examples 7-9 were prepared using an analogous process to that described in Examples 5 and 6 from either methyl 5-{4-[(1-cyclobutyl-4-piperidinyl)methyl]-1-piperidinyl}-2-pyrazinecarboxylate (may be prepared as described in Example 1) or methyl 5-(4-{[1-(1-methylethyl)-4-piperidinyl]methyl}-1-piperidinyl)-2-pyrazinecarboxylate (may be prepared as described in Example 2) and the amine indicated in the table below. All compounds displayed $^1$H-NMR and mass spectral data that were consistent with structure.

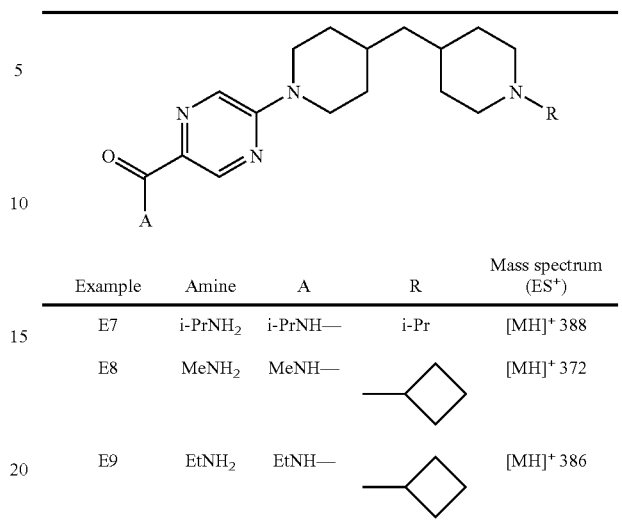

| Example | Amine | A | R | Mass spectrum (ES$^+$) |
|---|---|---|---|---|
| E7 | i-PrNH$_2$ | i-PrNH— | i-Pr | [MH]$^+$ 388 |
| E8 | MeNH$_2$ | MeNH— | ◇ | [MH]$^+$ 372 |
| E9 | EtNH$_2$ | EtNH— | ◇ | [MH]$^+$ 386 |

EXAMPLE 10

5-{4-[(1-Cyclobutyl-4-piperidinyl)methyl]-1-piperidinyl}-2-pyridinecarboxylic acid tris trifluoroacetate (E10)

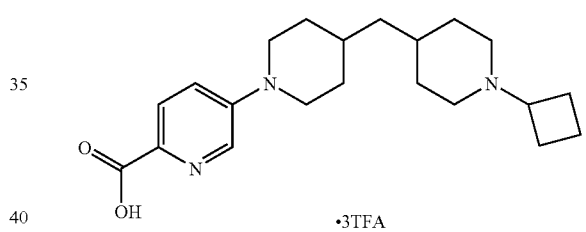

1,1-Dimethylethyl 5-{4-[(1-cyclobutyl-4-piperidinyl)methyl]-1-piperidinyl}-2-pyridinecarboxylate (may be prepared as described in Example 3) (0.23 g) was dissolved in aqueous trifluoroacetic acid (20 ml) and stirred at room temperature for 16 h. The reaction mixture was evaporated, then re-evaporated from toluene (3×10 ml) to afford the crude acid (E10) as a yellow solid (0.264 g). MS electrospray (+ion) 358 (MH$^+$)

EXAMPLE 11

5-{4-[(1-Cyclobutyl-4-piperidinyl)methyl]-1-piperidinyl}-N-methyl-2-pyridinecarboxamide (E11)

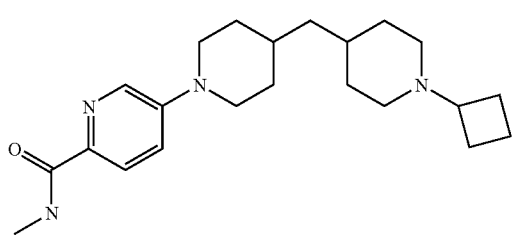

Step 1: 5{4-[(1-Cyclobutyl-4-piperidinyl)methyl]-1-piperidinyl}-2-pyridinecarbonyl chloride hydrochloride 5-{4-[(1-Cyclobutyl-4-piperidinyl)methyl]-1-piperidinyl}-2-pyridinecarboxylic acid tris trifluoroacetate (may be prepared as described in Example 10) (0.264 g) was dissolved in DCM (20 ml) with oxalyl chloride (0.2 ml) and dimethylformamide (1 drop). After 3 h the reaction mixture was evaporated and the resultant yellow foam re-evaporated from dichloromethane (3×20 ml) to give the crude acid chloride, which was used in the next step immediately.

Step 2: 5-{4-[(1-Cyclobutyl-4-piperidinyl)methyl]-1-piperidinyl}-N-methyl-2-pyridinecarboxamide 5-{4-[(1-Cyclobutyl-4-piperidinyl)methyl]-1-piperidinyl}-2-pyridinecarbonyl chloride hydrochloride (may be prepared as described in Example 11, step 1) was dissolved in dichloromethane (10 ml) and added dropwise to a stirred solution of methylamine (1.57 ml of a 2M solution in tetrahydrofuran) in dichloromethane (10 ml) cooled to 0° C. over 1 h. The reaction was allowed to stir for a further 3 h before the mixture was evaporated. Chromatography (silica gel, eluting with methanol/dichloromethane, 0-20%) afforded the title compound (E11) (0.13 g). MS electrospray (+ion) 371 (MH$^+$). $^1$H NMR δ (CDCl$_3$): 8.14 (1H, d, J=2.8 Hz), 8.01 (1H, d, J=8.8 Hz), 7.75 (1H, m), 7.19 (1H, dd, J=2.8, 8.8 Hz), 3.80 (2H, m), 3.00 (4H, m), 2.82 (3H, m), 2.19-1.21 (21H, m obscured by H$_2$O)

EXAMPLE 12

N-Methyl-5-(4-{[1-(1-methylethyl)-4-piperidinyl]methyl}-1-piperidinyl)-2-pyridinecarboxamide (E12)

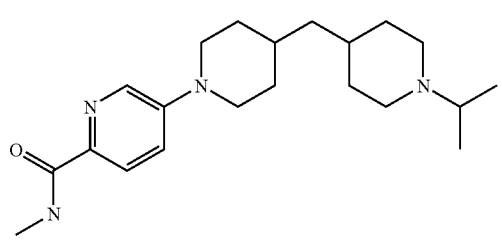

N-Methyl-5-(4-{[1-(1-methylethyl)-4-piperidinyl]methyl}-1-piperidinyl)-2-pyridinecarboxamide was prepared using an analogous process to that described in Examples 10 and 11 from 1,1-dimethylethyl 5-(4-{[1-(1-methylethyl)-4-piperidinyl]methyl}-1-piperidinyl)-2-pyridinecarboxylate (may be prepared as described in Example 4) and methylamine. The compound displayed $^1$H-NMR and mass spectral data that were consistent with structure. MS electrospray (+ion) 359 (MH$^+$).

EXAMPLE 13

1-(1-Methylethyl)-4-({1-[4-(3-methyl-1,2,4-oxadiazol-5-yl)phenyl]-4-piperidinyl}methyl)piperidine (E13)

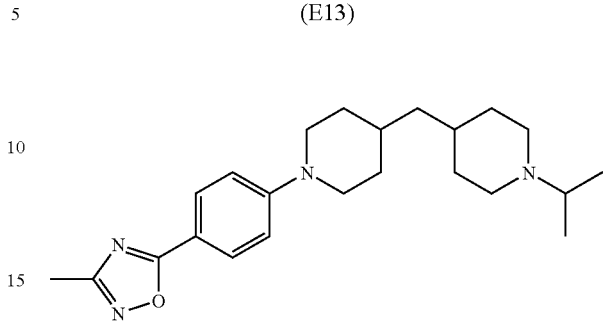

Sodium tert-butoxide (0.134 g) was added to a solution of 1-(1-methylethyl)-4-(4-piperidinylmethyl)piperidine (may be prepared as described in Description 4) (0.25 g), 5-(4-bromophenyl)-3-methyl-1,2,4-oxadiazole (may be prepared as described in Description 14) (0.223 g) and acetato(2'-di-tert-butylphosphino-1,1'-biphenyl-2-yl)palladium(II) (0.017 g) in toluene (30 ml). The reaction was heated under argon at 50° C. overnight then at 80° C. for a further 48 h, after which the reaction mixture was allowed to cool and was evaporated. Chromatography (silica gel, eluting with [2N NH$_3$ in methanol]/dichloromethane, 0-10%) afforded the oxadiazole which was further purified by passing through an SCX column (10 g, eluting with methanol [80 ml] then 2N NH$_3$ in methanol [80 ml]) to afford the title compound (E13) (0.080 g). MS electrospray (+ion) 383 (MH$^+$). $^1$H NMR δ (CDCl$_3$): 7.94 (2H, d, J=8.8 Hz), 6.92 (2H, d, J=9.2 Hz), 3.85 (2H, d, J=12.8 Hz), 2.88 (4H, m), 2.43 (3H, s), 2.10 (2H, m), 1.84-1.51 (7H, m), 1.42-1.17 (6H, m), 1.04 (6H, d, J=6.4 Hz)

EXAMPLE 14

1-[2-Fluoro-4-(3-methyl-1,2,4-oxadiazol-5-yl)phenyl]-4-{[1-(1-methylethyl)-4-piperidinyl]methyl}piperidine (E14)

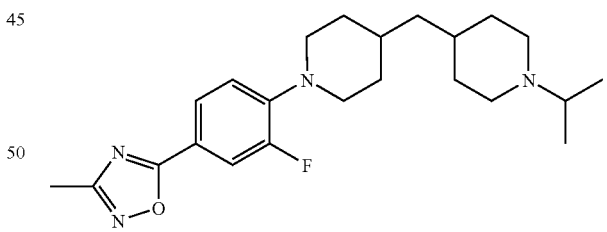

Sodium tert-butoxide (0.084 g) was added to a solution 1-(1-methylethyl)-4-(4-piperidinylmethyl)piperidine (may be prepared as described in Description 4) (0.156 g), 5-(4-bromo-3-fluorophenyl)-3-methyl-1,2,4-oxadiazole (may be prepared as described in Description 15) (0.150 g) and acetato (2'-di-tert-butylphosphino-1,1'-biphenyl-2-yl)palladium(II) (0.023 g) in toluene (10 ml). The reaction mixture was heated under argon at 80° C. overnight. After cooling to room temperature, the reaction mixture was passed through an SCX column (10 g, eluting with methanol [80 ml] then 2N NH$_3$ in methanol [80 ml]) to afford the title compound (E14) (0.065 g). MS electrospray (+ion) 401 (MH$^+$). $^1$H NMR δ (CDC$_{13}$): 7.79 (1H, dd, J=2, 8 Hz), 7.73 (1H, dd, J=2, 13.6 Hz), 7.00

(1H, t, J=8.6 Hz), 3.62 (2H, m), 2.90 (2H, m), 2.84-2.69 (3H, m), 2.44 (3H, s), 2.12 (2H, m), 1.77 (2H, m), 1.69 (2H, m), 1.56 (1H, m), 1.42-1.22 (7H, m), 1.05 (6H, d)

EXAMPLE 15

5-(4-{[1-(1-Methylethyl)-4-piperidinyl]methyl}-1-piperidinyl)-2-(3-methyl-1,2,4-oxadiazol-5-yl)pyridine (E15)

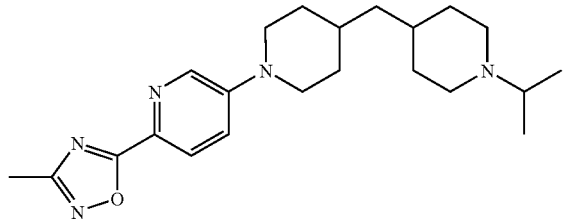

5-Bromo-2-(3-methyl-1,2,4-oxadiazol-5-yl)pyridine (maybe prepared as described in Description 17) (0.242 g) tris(dibenzylidineacetone)dipalladium(0) (0.055 g) and 2-dicyclohexylphosphino-2'-(N,N-dimethylamino)biphenyl (0.092 g) were added to degassed dioxane (5 ml). After 15 min 1-(1-methylethyl)-4-(4-piperidinylmethyl)piperidine (may be prepared as described in Description 4) (0.150 g) and sodium tert-butoxide (0.097 g) were added and the reaction mixture heated under argon at 90° C. for 6 h. After cooling to room temperature, the reaction mixture was passed through an SCX column (10 g, eluting with methanol [80 ml] then 2 N $NH_3$ in methanol [80 ml]) to afford the crude oxadiazole. Chromatography (silica gel, eluting with (2M $NH_3$/methanol)/dichloromethane, 0-20%) afforded the title compound (E15) (0.088 g).

MS electrospray (+ion) 384 (MH$^+$). $^1$H NMR δ (CDCl$_3$): 8.40 (1H, d, J=2.8 Hz), 7.98 (1H, d, J=8.8 Hz), 7.18 (1H, dd, J=2.8, 14.8 Hz), 3.89 (2H, app. d, J=13.2 Hz), 2.95-2.86 (4H, m), 2.69 (1H, sep, J=6.4 Hz), 2.47 (3H, s), 2.09 (2H, dt, J=2, 11.6 Hz), 1.83-1.80 (2H, m), 1.70-1.63 (2H, m), 1.37-1.17 (8H, m) and 1.04 (6H, d, J=6.4 Hz)

EXAMPLES 16-20 (E16-E20)

Examples 16 to 20 were prepared using an analogous process to that described in Example 15 from either 1-cyclobutyl-4-(4-piperidinylmethyl)piperidine (may be prepared as described in Description 6), 1-(1-methylethyl)-4-(4-piperidinylmethyl)piperidine (may be prepared as described in Description 4), 1-ethyl-4-(4-piperidinylmethyl)piperidine (may be prepared as described in Description 8), 1-(cyclopropylmethyl)-4-(4-piperidinylmethyl)piperidine (may be prepared as described in Description 10) or 1-methyl-4-(4-piperidinylmethyl)piperidine (D19) and 5-bromo-2-(3-methyl-1,2,4-oxadiazol-5-yl)pyridine (D17), 5-(4-bromo-2-fluorophenyl)-3-methyl-1,2,4-oxadiazole (D16) or 5-(4-bromophenyl)-3-methyl-1,2,4-oxadiazole (D14). Compounds displayed $^1$H-NMR and mass spectral data that were consistent with structure.

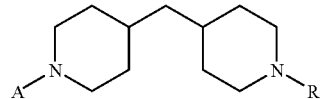

| Example | A | R | Mass spectrum (ES$^+$) |
|---|---|---|---|
| E16 | ![F-phenyl-oxadiazole] | i-Pr | [MH]$^+$ 401 |
| E17 | ![methyl-oxadiazole-pyridyl] | cyclobutyl | [MH]$^+$ 396 |
| E18 | ![methyl-oxadiazole-phenyl] | Et | [MH]$^+$ 369 |
| E19 | ![methyl-oxadiazole-phenyl] | CH$_2$-cyclopropyl | [MH]$^+$ 395 |
| E20 | ![methyl-oxadiazole-phenyl] | Me | [MH]$^+$ 355 |

EXAMPLE 21

5-(4-{[1-(1-Methylethyl)-4-piperidinyl]methyl}-1-piperidinyl)-2-pyridinecarbonitrile (E21)

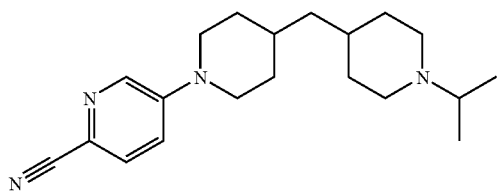

5-Bromo-2-pyridinecarbonitrile (0.49 g), tris(dibenzylidineacetone)dipalladium(0) (0.102 g) and 2-dicyclohexylphosphino-2'-(N,N-dimethylamino)biphenyl (0.132 g) were added to degassed DME (20 ml). After 15 min 1-(1-methylethyl)-4-(4-piperidinylmethyl)piperidine (may be prepared as described in Description 4) (0.5 g) and potassium phosphate (0.134 g) were added and the reaction mixture heated at 80° C. for 5 h. After cooling to room temperature, the reaction mixture was passed through an SCX column (20 g, eluting with methanol [80 ml] then 2N $NH_3$ in methanol [80 ml]) to afford the crude nitrile. Chromatography (silica gel, eluting with methanol/dichloromethane, 0-20%) afforded the title compound (E21) (0.3 g). MS electrospray (+ion) 327 (MH$^+$). $^1$H NMR δ (CDCl$_3$): 8.28 (1H, d, J=6.4 Hz), 7.47 (1H, d, J=8.8 Hz), 7.05 (1H, dd, J=3.2, 8.4 Hz), 3.85 (2H, m,), 2.94-2.87 (4H, m), 2.75 (1H, m), 2.14 (2H, m), 1.80 (2H, m), 1.71-1.58 (3H, m), 1.37-1.19 (7H, m), 1.06 (6H, d, J=6.8 Hz).

EXAMPLE 22

5-{4-[(1-Cyclobutyl-4-piperidinyl)methyl]-1-piperidinyl}-2-pyridinecarbonitrile (E22)

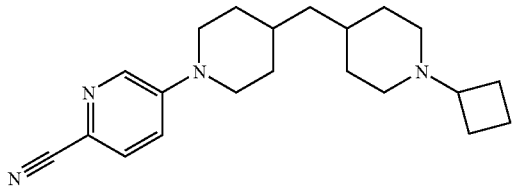

Example 22 was prepared using an analogous process to that described in Example 21 from 1-cyclobutyl-4-(4-piperidinylmethyl)piperidine (may be prepared as described in Description 6) and 5-bromo-2-pyridinecarbonitrile. The compound displayed $^1$H-NMR and mass spectral data that were consistent with structure. MS electrospray (+ion) 339 (MH$^+$).

EXAMPLE 23

1-{[5-(4-[1-(1-Methylethyl)-4-piperidinyl]methyl}-1-piperidinyl)-2-pyridinyl]ethanone (E23)

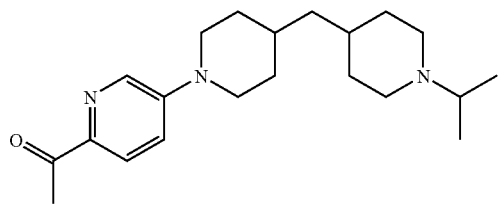

5-(4-{[1-(1-Methylethyl)-4-piperidinyl]methyl}-1-piperidinyl)-2-pyridinecarbonitrile (may be prepared as described in Example 21) (0.25 g) was dissolved in tetrahydrofuran (5 ml) and cooled to 0° C. MeMgBr (7.7 ml of 2M solution in diethyl ether) was added and the reaction mixture allowed to warm to room temperature for 3 h. Saturated ammonium chloride solution (10 ml) was added, the precipitate was removed by filtration and the mixture evaporated. The residue was dissolved in dichloromethane (2 ml), then chromatography (silica gel, eluting with [2 N NH$_3$ in methanol]/dichloromethane, 0-20%) afforded the title compound (E23) (0.045 g). MS electrospray (+ion) 344 (MH$^+$). $^1$H NMR δ (CDCl$_3$): 8.26 (1H, d, J=2.8 Hz), 7.93 (1H, d, J=8.8 Hz), 7.13 (1H, dd, J=3, 9 Hz), 3.85 (2H, m), 2.93-2.86 (4H, m), 2.69 (1H, m), 2.64 (3H, s), 2.10 (2H, m), 1.79 (2H, m), 1.66-1.57 (3H, m obscured by H$_2$O), 1.39-1.23 (7H, m), 1.05 (6H, d).

EXAMPLE 24

1-(5-{4-[(1-Cyclobutyl-4-piperidinyl)methyl]-1-piperidinyl}-2-pyridinyl)ethanone (E24)

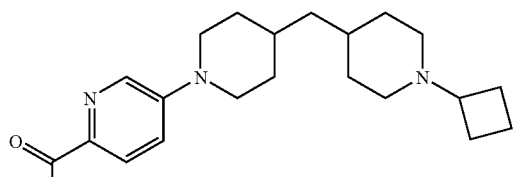

Example 24 was prepared using an analogous process to that described in Example 23 from 5-{4-[(1-Cyclobutyl-4-piperidinyl)methyl]-1-piperidinyl}-2-pyridinecarbonitrile (may be prepared as described in Example 22). $^1$H-NMR and mass spectral data were consistent with structure. MS electrospray (+ion) 356 (MH$^+$).

EXAMPLE 25

1-(4-{4-[(1-Cyclobutyl-4-piperidinyl)methyl]-1-piperidinyl}phenyl)ethanone (E25)

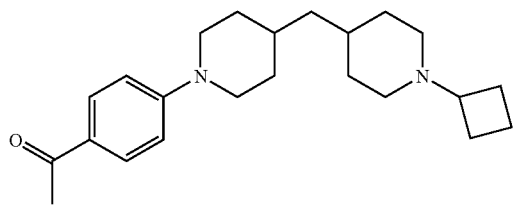

1-Cyclobutyl-4-(4-piperidinylmethyl)piperidine (may be prepared as described in Description 6) (0.15 g), 4-fluoroacetophenone (0.133 g) and potassium carbonate (0.177 g) were dissolved in DMSO (2 ml) and heated at 120° C. for 7 min in the microwave reactor. The crude reaction mixture was passed through an SCX column (10 g, eluting with methanol [80 ml] then 2 N NH$_3$ in methanol [80 ml]). Chromatography of the crude ketone (silica gel, eluting with methanol/dichloromethane, 0-25%) afforded the title compound (E25) (0.05 g). MS electrospray (+ion) 355 (MH$^+$).

EXAMPLES 26-32 (E26-E32)

Examples 26-32 were prepared using an analogous process to that described in Example 25 from either 1-cyclobutyl-4-(4-piperidinylmethyl)piperidine (may be prepared as described in Description 6), 1-(1-methylethyl)-4-(4-piperidinylmethyl)piperidine (may be prepared as described in Description 4), 1-ethyl-4-(4-piperidinylmethyl)piperidine (may be prepared as described in Description 8), 1-(cyclopropylmethyl)-4-(4-piperidinylmethyl)piperidine (may be prepared as described in Description 10) or 1-methyl-4-(4-piperidinylmethyl)piperidine (D19), and either 4-fluoroacetophenone, 2,2,2,4'-tetrafluoroacetophenone or 1-(6-chloro-3-pyridinyl)-1-ethanone. Compounds displayed $^1$H-NMR and mass spectral data that were consistent with structure.

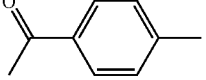

| Example | A | R | Mass spectrum (ES+) |
|---|---|---|---|
| E26 | 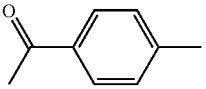 | i-Pr | [MH]+ 343 |
| E27 | 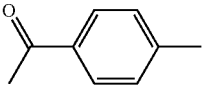 | Et | [MH]+ 329 |
| E28 |  | 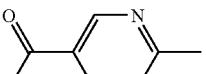 | [MH]+ 355 |
| E29 |  | 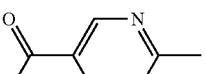 | [MH]+ 356 |
| E30 | 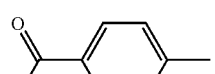 | i-Pr | [MH]+ 344 |
| E31 |  | 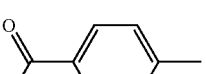 | [MH]+ 409 |
| E32 |  | Me | [MH]+ 315 |

EXAMPLES 33-34 (E33-E34)

Examples 33-34 were prepared using an analogous process to that described in Example 25 from either 1-cyclobutyl-4-(4-piperidinylmethyl)piperidine (may be prepared as described in Description 6) or 1-(1-methylethyl)-4-(4-piperidinylmethyl)piperidine (may be prepared as described in Description 4) and 3-chloro-6-trifluoromethylpyridazine (may be prepared as described in Goodman, Allan J.; Stanforth, Stephen P.; Tarbit, Brian. Tetrahedron (1999), 55(52), 15067-15070). Compounds displayed $^1$H-NMR and mass spectral data that were consistent with structure.

| Example | R | Mass spectrum (ES+) |
|---|---|---|
| E33 | i-Pr | [MH]+ 371 |
| E34 | cyclobutylmethyl | [MH]+ 383 |

EXAMPLE 35

5-{4-[(1-Cyclobutyl-4-piperidinyl)methyl]-1-piperidinyl}-2-(trifluoromethyl)pyrimidine (E35)

1-Cyclobutyl-4-(4-piperidinylmethyl)piperidine (may be prepared as described in Description 6) (0.15 g), 5-bromo-2-trifluoromethylpyrimidine (may be prepared as described in F. Cottet and M. Schlosser, Eur. J. Org. Chem., 2002, 327) (0.129 g), tris(dibenzylidineacetone)dipalladium(0) (0.053 g), 2-dicyclohexylphosphino-2'-(N,N-dimethylamino)biphenyl (0.088 g) and sodium tert-butoxide (0.092 g) were added to dioxane (2 ml) and heated at 120° C. for 14 min in the microwave reactor. The crude reaction mixture was passed through an SCX column (10 g, eluting with methanol [80 ml] then 2 N NH$_3$ in methanol [80 ml]). Chromatography (silica gel, eluting with methanol/dichloromethane, 0-20%) afforded the title compound (E35) (0.08 g). MS electrospray (+ion) 383 (MH+).

EXAMPLE 36

5-(4-{[1-(1-Methylethyl)-4-piperidinyl]methyl}-1-piperidinyl)-2-(trifluoromethyl)pyrimidine (E36)

Example 36 was prepared using an analogous process to that described in Example 35 from 1-(1-methylethyl)-4-(4-piperidinylmethyl)piperidine (may be prepared as described in Description 4) and 5-bromo-2-trifluoromethylpyrimidine (may be prepared as described in F. Cottet and M. Schlosser, Eur. J. Org. Chem., 2002, 327). $^1$H-NMR and mass spectral data were consistent with structure. MS electrospray (+ion) 371 (MH$^+$).

Abbreviations

BINAP 2,2'-bis(diphenylphosphino)-1,1'-binaphthyl
DCM dichloromethane
DME 1,2-dimethoxyethane
DMF N,N-dimethylformamide
DMSO dimethylsulfoxide
EtOAc ethyl acetate
h hour
min minutes
rt room temperature
TFA trifluoroacetic acid
THF tetrahydrofuran
SCX strong cation exchange
MP-NCO macroporous polystyrene isocyanate resin Biological Data A membrane preparation containing histamine H3 receptors may be prepared in accordance with the following procedures:

(i) Generation of Histamine H3 Cell Line

DNA encoding the human histamine H3 gene (Huvar, A. et al. (1999) Mol. Pharmacol. 55(6), 1101-1107) was cloned into a holding vector, pCDNA3.1 TOPO (InVitrogen) and its cDNA was isolated from this vector by restriction digestion of plasmid DNA with the enzymes BamH1 and Not-1 and ligated into the inducible expression vector pGene (InVitrogen) digested with the same enzymes. The GeneSwitch™ system (a system where in transgene expression is switched off in the absence of an inducer and switched on in the presence of an inducer) was performed as described in U.S. Pat. Nos.: 5,364,791; 5,874,534; and 5,935,934. Ligated DNA was transformed into competent DH5α E. coli host bacterial cells and plated onto Luria Broth (LB) agar containing Zeocin™ (an antibiotic which allows the selection of cells expressing the sh ble gene which is present on pGene and pSwitch) at 50 μg ml$^{-1}$. Colonies containing the re-ligated plasmid were identified by restriction analysis. DNA for transfection into mammalian cells was prepared from 250 ml cultures of the host bacterium containing the pGeneH3 plasmid and isolated using a DNA preparation kit (Qiagen Midi-Prep) as per manufacturers guidelines (Qiagen). CHO K1 cells previously transfected with the pSwitch regulatory plasmid (InVitrogen) were seeded at 2×10e6 cells per T75 flask in Complete Medium, containing Hams F12 (GIBCOBRL, Life Technologies) medium supplemented with 10% v/v dialysed foetal bovine serum, L-glutamine, and hygromycin (100 μg ml$^{-1}$), 24 hours prior to use. Plasmid DNA was transfected into the cells using Lipofectamine plus according to the manufacturers guidelines (InVitrogen). 48 hours post transfection cells were placed into complete medium supplemented with 500 μg ml$^{-1}$ Zeocin™.

10-14 days post selection 10 nM Mifepristone (InVitrogen), was added to the culture medium to induce the expression of the receptor. 18 hours post induction cells were detached from the flask using ethylenediamine tetra-acetic acid (EDTA; 1:5000; InVitrogen), following several washes with phosphate buffered saline pH 7.4 and resuspended in Sorting Medium containing Minimum Essential Medium (MEM), without phenol red, and supplemented with Earles salts and 3% Foetal Clone II (Hyclone). Approximately 1×10e7 cells were examined for receptor expression by staining with a rabbit polyclonal antibody, 4a, raised against the N-terminal domain of the histamine H3 receptor, incubated on ice for 60 minutes, followed by two washes in sorting medium. Receptor bound antibody was detected by incubation of the cells for 60 minutes on ice with a goat anti rabbit antibody, conjugated with Alexa 488 fluorescence marker (Molecular Probes). Following two further washes with Sorting Medium, cells were filtered through a 50 μm Filcon™ (BD Biosciences) and then analysed on a FACS Vantage SE Flow Cytometer fitted with an Automatic Cell Deposition Unit. Control cells were non-induced cells treated in a similar manner. Positively stained cells were sorted as single cells into 96-well plates, containing Complete Medium containing 500 μg ml$^{-1}$ Zeocin™ and allowed to expand before reanalysis for receptor expression via antibody and ligand binding studies. One clone, 3H3, was selected for membrane preparation.

(ii) Membrane Preparation from Cultured Cells

All steps of the protocol are carried out at 4° C. and with pre-cooled reagents. The cell pellet is resuspended in 10 volumes of homogenisation buffer (50 mM N-2-hydroxyethylpiperazine-N'-2-ethanesulfonic acid (HEPES), 1 mM ethylenediamine tetra-acetic acid (EDTA), pH 7.4 with KOH, supplemented with 10e-6M leupeptin (acetyl-leucyl-leucyl-arginal; Sigma L2884), 25 μg/ml bacitracin (Sigma B0125), 1 mM phenylmethylsulfonyl fluoride (PMSF) and 2×10e-6M pepstain A (Sigma)). The cells are then homogenised by 2×15 second bursts in a 1 liter glass Waring blender, followed by centrifugation at 500 g for 20 minutes. The supernatant is then spun at 48,000 g for 30 minutes. The pellet is resuspended in homogenisation buffer (4× the volume of the original cell pellet) by vortexing for 5 seconds, followed by homogenisation in a Dounce homogeniser (10-15 strokes). At this point the preparation is aliquoted into polypropylene tubes and stored at −80° C.

(iii) Generation of Histamine H1 Cell Line

The human H1 receptor was cloned using known procedures described in the literature [Biochem. Biophys. Res. Commun. 1994, 201(2), 894]. Chinese hamster ovary cells stably expressing the human Hi receptor were generated according to known procedures described in the literature [Br. J. Pharmacol. 1996, 117(6), 1071].

Compounds of the invention may be tested for in vitro biological activity in accordance with the following assays:

(I) Histamine H3 Functional Antagonist Assay (Method A)

For each compound being assayed, in a solid white 384 well plate, is added:

(a) 5 μl of test compound diluted to the required concentration in 10% DMSO (or 5 μl 10% DMSO as a control); and (b) 30 μl bead/membrane/GDP mix prepared by mixing Wheat Germ Agglutinin Polystyrene LeadSeeker® (WGA PS LS) scintillation proximity assay (SPA) beads with membrane (prepared in accordance with the methodology described above) and diluting in assay buffer (20 mM N-2-Hydroxyethylpiperazine-N'-2-ethanesulfonic acid (HEPES)+100 mM NaCl+10 mM MgCl$_2$, pH7.4 NaOH) to give a final volume of 30 μl which contains 5 μg protein and 0.25 mg bead per well, incubating at 4° C. for 30 minutes on a roller and, just prior to addition to the plate, adding 10 μM final concentration of guanosine 5' diphosphate (GDP) (Sigma; diluted in assay buffer).

The plates were then incubated at room temperature for 30 minutes on a shaker followed by addition of:

(c) 15 μl 0.38 nM [$^{35}$S]-GTPγS (Amersham; Radioactivity concentration=37 MBq/ml; Specific activity=1160 Ci/mmol), histamine (at a concentration that results in the final assay concentration of histamine being $EC_{80}$).

After 2-6 hours, the plate is centrifuged for 5 min at 1500 rpm and counted on a Viewlux counter using a 613/55 filter for 5 min/plate. Data is analysed using a 4-parameter logistical equation. Basal activity used as minimum i.e. histamine not added to well.

(II) Histamine H3 Functional Antagonist Assay (Method B)

For each compound being assayed, in a solid white 384 well plate, is added:

(a) 0.5 μl of test compound diluted to the required concentration in DMSO (or 0.5 μl DMSO as a control);
(b) 30 μl bead/membrane/GDP mix prepared by mixing Wheat Germ Agglutinin Polystyrene LeadSeeker® (WGA PS LS) scintillation proximity assay (SPA) beads with membrane (prepared in accordance with the methodology described above) and diluting in assay buffer (20 mM N-2-Hydroxyethylpiperazine-N'-2-ethanesulfonic acid (HEPES)+100 mM NaCl+10 mM $MgCl_2$, pH7.4 NaOH) to give a final volume of 30 μl which contains 5 μg protein and 0.25 mg bead per well, incubating at room temperature for 60 minutes on a roller and, just prior to addition to the plate, adding 10 μM final concentration of guanosine 5' diphosphate (GDP) (Sigma; diluted in assay buffer);
(c) 15 μl 0.38 nM [$^{35}$S]-GTPγS (Amersham; Radioactivity concentration=37MBq/ml; Specific activity=1160 Ci/mmol), histamine (at a concentration that results in the final assay concentration of histamine being $EC_{80}$).

After 2-6 hours, the plate is centrifuged for 5 min at 1500 rpm and counted on a Viewlux counter using a 613/55 filter for 5 min/plate. Data is analysed using a 4-parameter logistical equation. Basal activity used as minimum i.e. histamine not added to well.

(II) Histamine H1 Functional Antagonist Assay

The histamine H1 cell line was seeded into non-coated black-walled clear bottom 384-well tissue culture plates in alpha minimum essential medium (Gibco/Invitrogen, cat no. 22561-021), supplemented with 10% dialysed foetal calf serum (Gibco/Invitrogen cat no. 12480-021) and 2 mM L-glutamine (Gibco/Invitrogen cat no 25030-024) and maintained overnight at 5% $CO_2$, 37° C.

Excess medium was removed from each well to leave 10 μl. 30 μl loading dye (250 μM Brilliant Black, 2 μM Fluo-4 diluted in Tyrodes buffer+probenecid (145 mM NaCl, 2.5 mM KCl, 10 mM HEPES, 10 mM D-glucose, 1.2 mM $MgCl_2$, 1.5 mM $CaCl_2$, 2.5 mM probenecid, pH adjusted to 7.40 with NaOH 1.0 M)) was added to each well and the plates were incubated for 60 minutes at 5% $CO_2$, 37° C.

10 μl of test compound, diluted to the required concentration in Tyrodes buffer+probenecid (or 10 μl Tyrodes buffer+probenecid as a control) was added to each well and the plate incubated for 30 min at 37° C., 5% $CO_2$. The plates were then placed into a FLIPR™ (Molecular Devices, UK) to monitor cell fluorescence ($\lambda_{ex}$=488 nm, $\lambda_{EM}$=540 nm) in the manner described by Sullivan et al. (In: Lambert DG (ed.), Calcium Signaling Protocols, New Jersey: Humana Press, 1999, 125-136) before and after the addition of 10 μl histamine at a concentration that results in the final assay concentration of histamine being $EC_{80}$.

Functional antagonism is indicated by a suppression of histamine induced increase in fluorescence, as measured by the FLIPR™ system (Molecular Devices). By means of concentration effect curves, functional affinities are determined using standard pharmacological mathematical analysis.

Results

The compounds of Examples E6-E7 and E12-E13 were tested in the histamine H3 functional antagonist assay (method A). The results are expressed as functional $pK_i$ ($fpK_i$) values. A functional $pK_i$ is the negative logarithm of the antagonist equilibrium dissociation constant as determined in the H3 functional antagonist assay using membrane prepared from cultured H3 cells. The results given are averages of a number of experiments. These compounds exhibited antagonism $\geq$8 $fpK_i$. More particularly the compounds of Example E6 and E12-13 exhibited antagonism $\geq$9.0 $fpK_i$. Even more particularly, the compound of Example E13 exhibited antagonism $\geq$9.5 $fpK_i$.

The compounds of Examples E8-E9, E11-E12 and E14-36 were tested in the histamine H3 functional antagonist assay (method B). Again, the results are expressed as functional $pK_i$ ($fpK_i$) values and are averages of a number of experiments. These compounds exhibited antagonism $\geq$8 $fpK_i$. More particularly the compounds of Examples E8-E9, E11-12, E14-18, E21-27, E29, E31 and E34 exhibited antagonism $\geq$9.0 $fpK_i$. Even more particularly, the compounds of Examples E16, E18, E22 and E24 exhibited antagonism $\geq$9.5 $fpK_i$.

The compounds of Examples E6-E9 and E11-E36 were tested in the histamine H1 functional antagonist assay. The results are expressed as functional $pK_i$ ($fpK_i$) values and are averages of a number of experiments. The functional $pK_i$ may be derived from the negative logarithm of the $pIC_{50}$ (concentration producing 50% inhibition) in the H1 functional antagonist assay according to the Cheng-Prusoff equation (Cheng, Y. C. and Prusoff, W. H., 1973, Biochem. Pharmacol. 22, 3099-3108.). All compounds tested exhibited antagonism <6.0 $fpK_i$.

What is claimed is:

1. A compound of formula (I) or a pharmaceutically acceptable salt thereof:

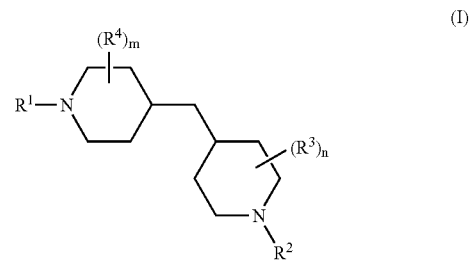

(I)

wherein:
$R^1$ represents heteroaryl, wherein said heteroaryl group of $R^1$ may be optionally substituted by one or more substituents which may be the same or different, and which are selected from the group consisting of halogen, hydroxy, cyano, nitro, oxo, halo$C_{1-6}$ alkyl, polyhalo$C_{1-6}$ alkyl, halo$C_{1-6}$ alkoxy, polyhalo$C_{1-6}$ alkoxy, $C_{1-6}$ alkyl, $C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, $C_{1-6}$ alkylsulfonamido$C_{1-6}$ alkyl, $C_{1-6}$ alkylamido$C_{1-6}$ alkyl, phenyl, phenylsulfonyl, phenylsulfonyloxy, phenyloxy, phenylsulfonamido, phenylcarboxamido, phenoyl, or a group —$COR^{15}$, —$COOR^{15}$, —$NR^{15}R^{16}$, —$CONR^{15}R^{16}$, —$NR^{15}COR^{16}$, —NR$^{15}$SO$_2$R$^{16}$ or —SO$_2$NR$^{15}$R$^{16}$, wherein R$^{15}$ and R$^{16}$ independently represent hydrogen, C$_{1-6}$ alkyl, haloC$_{1-6}$ alkyl, polyhaloC$_{1-6}$ alkyl or C$_{3-6}$ cycloalkyl or together form a heterocyclic ring;

R$^2$ represents C$_{1-8}$ alkyl, C$_{3-6}$ alkenyl, C$_{3-6}$ alkynyl, C$_{3-6}$ cycloalkyl, C$_{5-6}$ cycloalkenyl or —C$_{1-4}$alkyl-C$_{3-6}$ cycloalkyl;

wherein said C$_{3-6}$ cycloalkyl groups of R$^2$ may be optionally substituted by one or more substituents which may be the same or different, and which are selected from the group consisting of halogen, C$_{1-4}$ alkyl or polyhaloC$_{1-6}$ alkyl groups;

each R$^3$ and R$^4$ group independently represents C$_{1-4}$ alkyl;

m and n both represent 0.

2. The compound according to claim 1, wherein R$^2$ represents C$_{1-8}$ alkyl, C$_{3-6}$ cycloalkyl or C$_{1-4}$alkyl-C$_{3-6}$cycloalkyl.

3. The compound according to claim 1 which is:

methyl 5-{4-[(1-cyclobutyl-4-piperidinyl)methyl]-1-piperidinyl}-2-pyrazinecarboxylate;

methyl 5-(4-{[1-(1-methylethyl)-4-piperidinyl]methyl}-1-piperidinyl)-2-pyrazinecarboxylate;

1,1-dimethylethyl 5-{4-[(1-cyclobutyl-4-piperidinyl)methyl]-1-piperidinyl}-2-pyridinecarboxylate;

1,1-dimethylethyl 5-(4-{[1-(1-methylethyl)-4-piperidinyl]methyl}-1-piperidinyl)-2-pyridinecarboxylate;

5-{4-[(1-cyclobutyl-4-piperidinyl)methyl]-1-piperidinyl}-2-pyrazinecarboxylic acid;

5-{4-[(1-cyclobutyl-4-piperidinyl)methyl]-1-piperidinyl}-N-(1-methylethyl)-2-pyrazinecarboxamide;

N-(1-methylelthyl)-5-(4-{[1-(1-methylethyl)-4-piperidinyl]methyl}-1-piperidinyl)-2-pyrazinecarboxamide;

5-{4-[(1-cyclobutyl-4-piperidinyl)methyl]-1-piperidinyl}-N-methyl-2-pyrazinecarboxamide;

5-{4-[(1-cyclobutyl-4-piperidinyl)methyl]-1-piperidinyl}-N-ethyl-2-pyrazinecarboxamide;

5-{4-[(1-cyclobutyl-4-piperidinyl)methyl]-1-piperidinyl}-2-pyridinecarboxylic acid;

5-{4-[(1-cyclobutyl-4-piperidinyl)methyl]-1-piperidinyl}-N-methyl-2-pyridinecarboxamide;

N-methyl-5-(4-{[1-(1-methylethyl)-4-piperidinyl]methyl}-1-piperidinyl)-2-pyridinecarboxamide; 5-(4-{[1-(1-methylethyl)-4-piperidinyl]methyl}-1-piperidinyl)-2-(3-methyl-1,2,4-oxadiazol-5-yl)pyridine;

5-{4-[(1-cyclobutyl-4-piperidinyl)methyl]-1-piperidinyl}-2-(3-methyl-1,2,4-oxadiazol-5-yl) pyridine;

5-(4-{[1-(1-methylethyl)-4-piperidinyl]methyl}-1-piperidinyl)-2-pyridinecarbonitrile; 5-{4-[(1-cyclobutyl-4-piperidinyl)methyl]-1-piperidinyl}-2-pyridinecarbonitrile;

1-[5-(4-{[1-(1-methylethyl)-4-piperidinyl]methyl}-1-piperidinyl)-2-pyridinyl]ethanone;

1-(5-{4-[(1-cyclobutyl-4-piperidinyl)methyl]-1-piperidinyl}-2-pyridinyl)ethanone;

1-(6-{4-[(1-cyclobutyl-4-piperidinyl)methyl]-1-piperidinyl}-3-pyridinyl)ethanone;

1-[6-(4-{[1-(1-methylethyl)-4-piperidinyl]methyl}-1-piperidinyl)-3-pyridinyl]ethanone;

3-(4-{[1-(1-methylethyl)-4-piperidinyl]methyl}-1-piperidinyl)-6-(trifluoromethyl) pyridazine;

3-{4-[(1-cyclobutyl-4-piperidinyl)methyl]-1-piperidinyl}-6-(trifluoromethyl)pyridazine;

5-{4-[(1-cyclobutyl-4-piperidinyl)methyl]-1-piperidinyl}-2-(trifluoromethyl)pyrimidine;

5-(4-{[1-(1-methylethyl)-4-piperidinyl]methyl}-1-piperidinyl)-2-(trifluoromethyl)pyrimidine;

or a pharmaceutically acceptable salt thereof.

4. A pharmaceutical composition which comprises a compound of claim 1 or a pharmaceutically acceptable salt thereof and a pharmaceutically acceptable carrier or excipient.

* * * * *